(12) United States Patent
Wu et al.

(10) Patent No.: US 10,663,446 B2
(45) Date of Patent: May 26, 2020

(54) METHODS, SYSTEMS AND DEVICES FOR BATCH SAMPLING

(71) Applicants: FREMONTA Corporation, Fremont, CA (US); THE UNITED STATES OF AMERICA AS REPRESENTED BY THE SECRETARY OF AGRICULTURE, Washington, DC (US)

(72) Inventors: Florence Wu, Milpitas, CA (US); Yongqing Huang, Newark, CA (US); Terrance Arthur, Hastings, NE (US); Tommy Wheeler, Clay Center, NE (US)

(73) Assignees: FREMONTA Corporation, Fremont, CA (US); THE UNITED STATES OF AMERICA AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 541 days.

(21) Appl. No.: 14/625,308

(22) Filed: Feb. 18, 2015

(65) Prior Publication Data

US 2015/0241401 A1    Aug. 27, 2015

Related U.S. Application Data

(60) Provisional application No. 61/941,418, filed on Feb. 18, 2014.

(51) Int. Cl.
*G01N 33/12* (2006.01)
*G01N 1/04* (2006.01)
(Continued)

(52) U.S. Cl.
CPC ............. *G01N 33/12* (2013.01); *G01N 1/02* (2013.01); *G01N 1/04* (2013.01); *G01N 1/20* (2013.01);
(Continued)

(58) Field of Classification Search
USPC .................................................. 422/65–68.1
See application file for complete search history.

(56) References Cited

U.S. PATENT DOCUMENTS

| 3,370,175 A | * | 2/1968 | Jordon | ................... C12Q 1/18 |
| | | | | 324/99 R |
| 4,848,165 A | | 7/1989 | Bartilson et al. | |

(Continued)

FOREIGN PATENT DOCUMENTS

| CA | 2859111 A1 | 6/2013 |
| EP | 2604120 A1 | 6/2013 |

OTHER PUBLICATIONS

International Search Report and Written Opinion dated Jun. 29, 2015, from International Application No. PCT/US2015/016384 (12 pages).

*Primary Examiner* — Brian R Gordon
(74) *Attorney, Agent, or Firm* — Kilpatrick Townsend & Stockton LLP

(57) ABSTRACT

Systems and methods for sampling within a conveyance system are provided herein, such systems and methods being particularly useful in batch sampling of food products for a targeted biological agent. In one aspect, the sampling system includes a conveyance system and one or more sampling devices positioned along a conveyance path such that at least one portion of the batch contacts a sampling medium of the one or more sampling devices. In another aspect, sampling devices are provided that allow a sampling member to be secured in a sampling position for batch testing and readily removed after sampling and tested. The systems, devices (Continued)

and methods herein provide improved sampling coverage of the entire batch and reduce waste and inefficiency as compared to conventional batch sampling methods.

38 Claims, 21 Drawing Sheets

(51) Int. Cl.
  *G01N 35/02* (2006.01)
  *G01N 1/20* (2006.01)
  *G01N 1/02* (2006.01)

(52) U.S. Cl.
  CPC ....... *G01N 35/02* (2013.01); *G01N 2001/028* (2013.01)

(56) References Cited

U.S. PATENT DOCUMENTS

| | | | |
|---|---|---|---|
| 5,243,865 A | 9/1993 | Hsu et al. | |
| 5,554,537 A | 9/1996 | Sharpe | |
| 5,811,137 A * | 9/1998 | Clark | A21C 3/02 |
| | | | 100/168 |
| 6,207,406 B1 | 3/2001 | Wilkins | |
| 6,720,191 B1 | 4/2004 | Goldstein et al. | |
| 7,697,966 B2 * | 4/2010 | Monfre | A61B 5/061 |
| | | | 600/310 |
| 2002/0157613 A1 * | 10/2002 | Phelps | A01K 45/00 |
| | | | 119/6.8 |
| 2011/0006140 A1 * | 1/2011 | Ishizaki | B65B 1/08 |
| | | | 241/24.1 |
| 2014/0099656 A1 * | 4/2014 | Krebs | C12Q 1/32 |
| | | | 435/26 |
| 2015/0049134 A1 * | 2/2015 | Shmaiser | G03G 15/238 |
| | | | 347/1 |

* cited by examiner

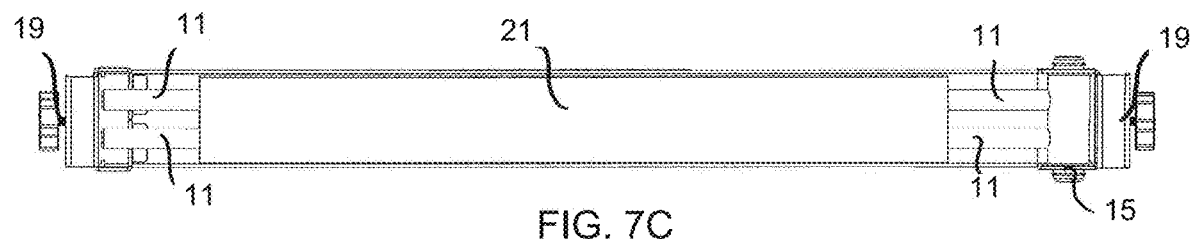
FIG. 7C
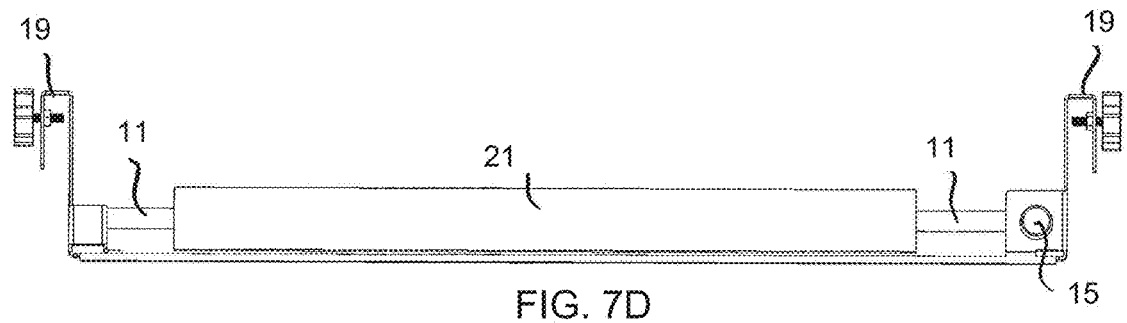
FIG. 7D
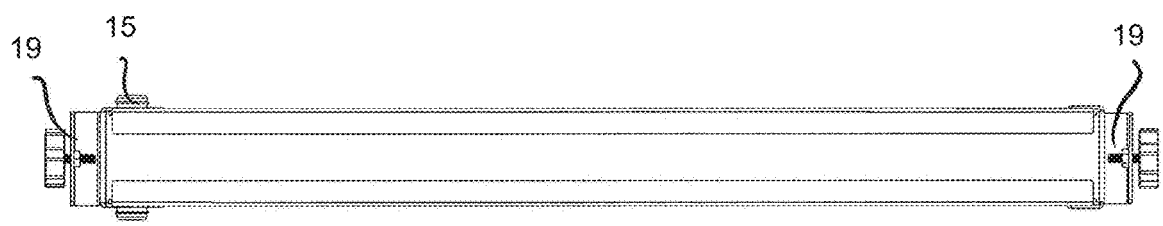
FIG. 7E
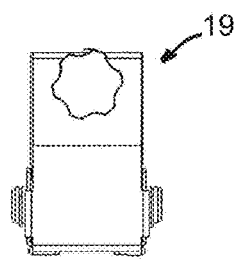 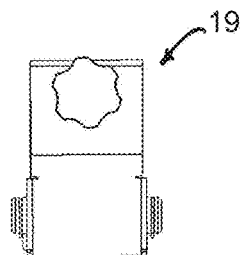
FIG. 7F	FIG. 7G

SECTION B-B

```
┌─────────────────────────────────────┐
│ Removably attached a sampling member│
│ comprising a compressed, dried      │
│ cellulose sheet member to a support │
│ plate                               │
└─────────────────────────────────────┘
                  ↓
┌─────────────────────────────────────┐
│ Securing the support plate with the │
│ sampling member mounted thereon to  │
│ a base plate affixed to a conveyor  │
│ such that the sampling member is    │
│ disposed along the conveyance path  │
│ of the conveyor so as to contact    │
│ products conveyed along the path    │
│ for sampling                        │
└─────────────────────────────────────┘
                  ↓
┌─────────────────────────────────────┐
│ Conveying a product stream along the│
│ conveyance path until an entire     │
│ batch has been conveyed, then       │
│ removing the sample member from the │
│ support plate                       │
└─────────────────────────────────────┘
                  ↓
┌─────────────────────────────────────┐
│ Inserting the removed sampling      │
│ medium into a sample container along│
│ with a nutrient broth               │
└─────────────────────────────────────┘
                  ↓
┌─────────────────────────────────────┐
│ Culturing for a targeted biological │
│ agent by maintaining the sample     │
│ medium in the broth within a        │
│ temperature range for a duration    │
│ suitable for incubation of the      │
│ targeted biological agent           │
└─────────────────────────────────────┘
                  ↓
┌─────────────────────────────────────┐
│ Identifying/testing the culture for │
│ the biological agent to determine   │
│ the presence of the biological agent│
│ in the batch                        │
└─────────────────────────────────────┘
```

FIG. 20

METHODS, SYSTEMS AND DEVICES FOR BATCH SAMPLING

CROSS-REFERENCES TO RELATED APPLICATIONS

The present application is a non-provisional of and claims the benefit of U.S. Provisional Patent Application No. 61/941,418, filed Feb. 18, 2014, the entire contents of which are incorporated herein by reference.

BACKGROUND

Production of animal food products is an example of batch processing. Meats from farm animals, such as beef and chicken, are produced by breaking down a slaughtered animal carcass into basic lots to be shipped to retailers and sold to consumers. At various stages of the slaughtering and butchering process, pathogens may contaminate a portion of the animal meat product, which may cause other cuts of meat to become contaminated upon contact with the contaminated meat product or associated liquid. Pathogens, such as bacterium E. coli, are natural inhabitants of an animal's gastrointestinal (GI) tract. While severing of the GI tract is generally avoided during slaughter and butcher, occasionally accidental severing or rupture of the GI tract during processing causes contamination of the animal meat product. This in turn may cause contamination of other meat cuts that come into contact with the contaminated meat or with liquid that contacts the contaminated meat.

The bacterium E. coli resides in the gastrointestinal (GI) tract of most warm-blooded animals, including humans and cattle. Although over 200 strains of E. coli have been identified, certain strains are known food borne pathogens causing diseases ranging from diarrhea to the potentially deadly hemorrhagic colitis/hemolytic uremic syndrome. Red meat, such as beef has been identified as prominent sources of enterovirulent E. coli. One particular strain, enterovirulent E. coli is O157:H7, is considered as an adulterant in certain beef products by the USDA. Meat that is found to be contaminated with E. coli O157:H7 is not suitable for human consumption and must be destroyed or subjected to a validated cook process to kill E. coli O157:H7. Meat that tests negative for E. coli O157:H7 is generally packaged and sent to suppliers, supermarkets and other meat distribution businesses for further processing or sale to consumers.

BRIEF SUMMARY

This invention relates to batch sampling for detection of a targeted agent within a batch of products. The targeted agent may be a chemical agent (e.g., a small molecule or macromolecule, which may exhibit a certain functional feature such as toxicity or explosive nature) or a biological agent (e.g., a pathogen, microbe, plant or animal matter). In one particular example, the present invention relates to the sampling of pathogens, such as E. coli, within beef trimmings. It is appreciated however that sampling devices in accordance with the invention may be used for batch sampling of any number of products, for example, sampling of harmful or dangerous substances such as explosives or biohazard-contaminated material in the luggage or cargo being loaded onto a vehicle of transportation such as a plane, train, ship/boat, and the like.

To reduce the pathogen content of beef products, various segments of the beef industry spend millions of dollars annually on pathogen testing. Among conventional testing methods currently used in the beef industry, the best sampling procedure for testing beef trimmings is the N=60 method. However, N=60 provides a relatively small sample of the trim from each ~2000 lb combo bin and the sample is generally taken only from the top of the combo, which leaves much of the trim in a given combo bin unsampled. Moreover, an unacceptable amount of ground beef still tests positive for E. coli O157:H7 even after negative trim tests. Since the sampled beef is destroyed during the testing procedure, significant increases in sampling to improve sampling coverage may result in unacceptably high volume of product being destroyed. In addition, current sampling methods are somewhat labor intensive, particularly when sampling relatively larger meat trimmings which must be broken down to accommodate sampling processes.

In view of the above noted drawbacks associated with conventional sampling methods used in beef production, it would be desirable to provide sampling methods and devices that allow for identification and removal of a greater percentage of contaminated meat from commerce, as well as improve cost, ease and efficiency of sampling. In particular, sampling methods and devices are needed that provide improved coverage of products of each batch and improved accuracy in sampling, while avoiding unnecessary removal and destruction of uncontaminated product.

In certain aspects, the system includes a conveyance system that conveys a batch having one or more items along a conveyance path and one or more sampling devices positioned within the conveyance path so that the sampling devices sample at least some or one portion of the batch during conveyance. The sampling device may include a sampling member comprising a sampling medium and a sampling device body to which the sampling member is releasably attached. The sampling device supports the sampling member in a sampling position so that the sampling medium contacts at least one portion of the batch during conveyance. The sampling medium includes a surface that retains a solid and/or liquid residue of at least one portion of the batch upon contact. In some embodiments, the sampling medium comprises a bunch of sampling filaments, a sampling roller, or one or more sponges. In certain embodiments, the sampling medium is an approved food contact material such as cellulose sheet. In one aspect, a cellulose sheet encompasses a porous, soft and compressible material, for example a sponge-like material. In many embodiments, the cellulose sheet comprises wood pulp and vegetal fibers. In most embodiments the sampling medium will be sterilized by conventional means but it is only required that it be free of the organisms or agents of interest. The attachment feature of the sampling member may include an adhesive and/or a passageway for receiving an associated support component of the sampling device. The support component may include one or more rods or shafts for insertion into the corresponding passageways of the sampling member. The shafts may be movable or pivot upwards to facilitate easy removal and replacement of the sampling medium after sampling of each batch. In some embodiments, the sampling member is an elongate sponge, for example, a rectangular sponge about 24 inches in length, that extends substantially across the conveyance path, such as when attached to the front end of a conveyor belt of the conveyance system so as to contact at least some or one portion of the batch as it is transported by the conveyor belt for batch collection.

Methods in accordance with embodiments of the invention includes batch sampling for a targeted agent that can be applied to a variety of differing industries for use in detection of targeted agents. In certain embodiments, the method includes removably attaching a sampling device within a conveyance system at a sampling position; conveying a batch comprising at least one item, often multiple items, along a conveyance path such that at least a portion of the batch contacts a sampling medium of the sampling device during conveyance; removing the sampling medium from the conveyance system after contact with at least a portion of the batch and testing for the targeted agent using the sampling medium to assess a presence of the targeted agent within the batch. In some embodiments, the targeted agent is a biological agent, including various pathogens such as *E. coli* and the batch includes a batch of food products, including meat trimmings, such as beef. In such embodiments, testing may include culturing of the biological agent and identification of the agent from the culture.

The above systems, devices and methods are described further in the following figures and descriptions, but are not limited thereto.

BRIEF DESCRIPTION OF THE DRAWINGS

FIGS. 7A-7G illustrate various views of an example sampling member in accordance with embodiments of the invention;

FIGS. 17-20 schematically illustrate methods of sampling in accordance with embodiments of the invention.

DETAILED DESCRIPTION

Figure 1:
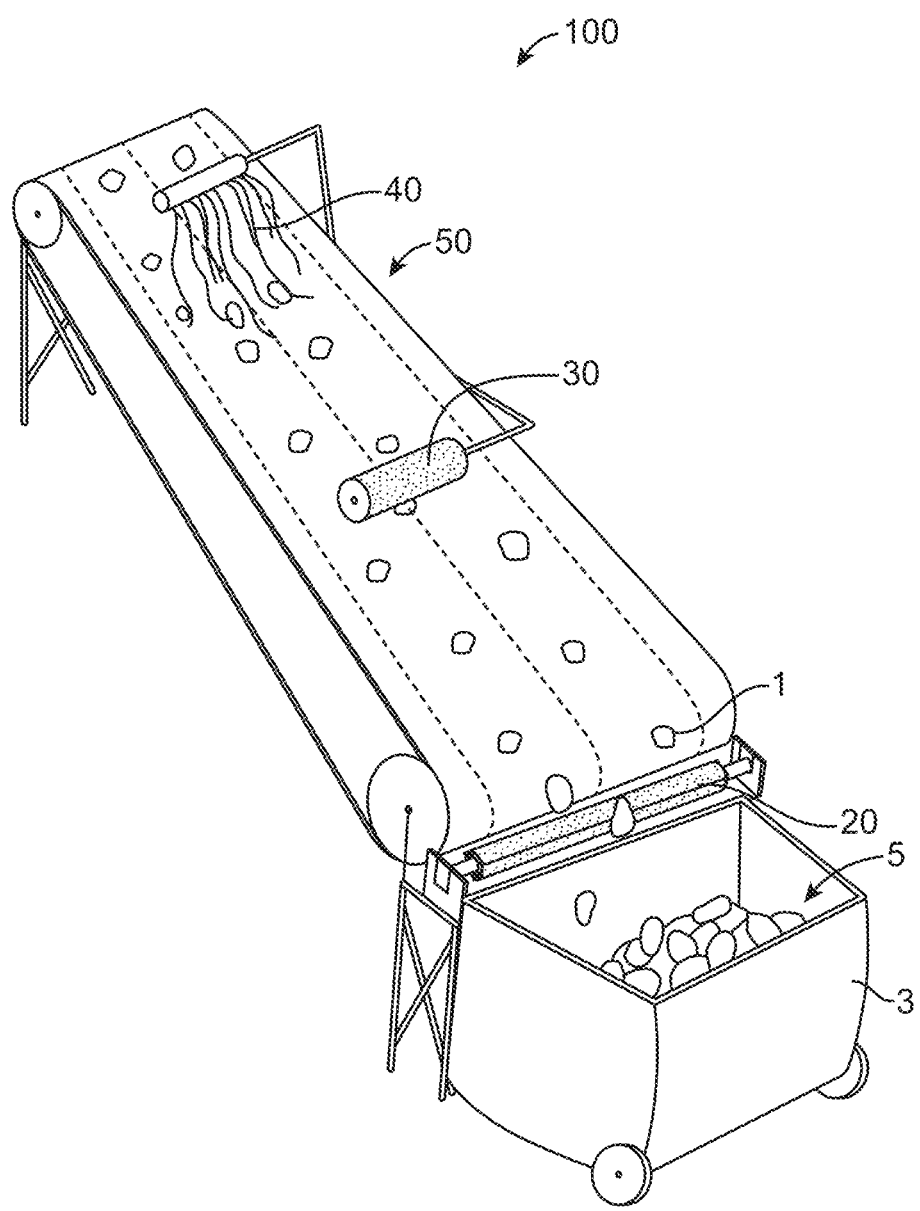
FIG. 1 is an overview illustration of a batch processing/sampling system in accordance with embodiments of the invention.

Embodiments of the invention relate to batch sampling for detection of a targeted agent, in particular, embodiments of the invention described herein are well suited for detecting the presence of biological agents within animal food products, such as detection of pathogens in a batch of meat trimmings.

To provide improved coverage of the material being sampled from each batch of items, embodiments of the invention utilize one or more sampling devices in conjunction with a conveyance system used for collection of each batch. In one aspect, the one or more sampling devices are positioned along the conveyance path along which one or more items from each batch are conveyed before being collected. For example, in collection of a batch of meat trimming, the conveyance system may comprise a conveyor belt along which the beef trimmings are transported before being collected in a combo bin positioned at the back end of the conveyor belt. The sampling devices generally include a sampling member having a medium that retains a liquid or solid residue from the items or beef trimmings upon contact with the sampling medium so that once the batch has been collected, the sampling medium can be removed from the conveyance system and tested for the presence of the targeted agent. Each sampling member is associated with a particular batch so that should testing require additional time, if testing indicates the presence of the targeted agent, the batch can be intercepted and removed from production or commerce. This aspect allows for testing using methods that may provide higher confidence levels, albeit longer testing time, without unnecessarily slowing the transport of the items or beef trimmings within the production process. The sampling member is configured to be easily removable and replaceable so as to simplify sampling of each batch and improve ease of use. Advantageously, this approach provides improved coverage of the batch of products, improves ease and efficiency in sampling and avoids destruction of uncontaminated product. Another advantage of these sample collection devices is that they may be used with existing conveyance systems, including conveyer belts, chutes and turntables.

In one aspect, the system and methods including a sampling device comprising a sampling medium having a sampling surface that retains a liquid or solid residue as the surface contacts one or more items in a batch. Although typically, the sampling surface includes a porous surfaced material, such as a sponge, cloth or gauze, it is appreciated that, depending on the application, various other types of surfaces may be used to retain residue for use as samples (e.g., an adhesive tape, fine mesh, coarse surface). In one aspect, it may be desirable for the sampling surface to retain moisture so that during the course of sampling, any liquid residue retained does not dry out, such that any biological agents would remain viable for subsequent testing. For this reason, for some applications, the sampling surface may further include a moisture providing component, such as a gel layer or liquid retaining material. In another aspect, it may be desirable for the sampling medium to be an approved food contact surface such as a cellulose sponge without biocides.

In certain embodiments, the sampling device includes a sampling member, comprising the sampling medium described above, and an attachment feature for releasably attaching the sampling member in a sampling position within a conveyance system. The sampling position is such that at least one portion of the batch conveyed by the conveyance system contacts the sampling medium of the device. The sampling member may itself be comprised entirely of the sampling medium (e.g. the sponge) or may include an additional component for supporting the sampling medium (e.g. substrate or roller body). As can be understood by referring to FIGS. 1-7G, the sampling devices may be configured in various different ways, for example as a sampling sponge fixedly attached to the conveyance system, a sampling roller, or a bunch of sampling filaments that extend into the conveyance path along which the items are transported.

FIG. 1 illustrates an embodiment in which three different sampling devices are utilized in a single conveyance system for transporting beef trimmings. The conveyance system comprises a conveyer belt that transports one or more items for collection in a batch. In this example, the sampling conveyance system 100 includes a conveyor belt 50 that transports beef trimmings 1 for collection as a batch 5 in a combo bin 3 positioned at the front end of the conveyor belt 50. Three different types of sampling devices are illustrated—an elongate sampling member 20 on the front end of the conveyor across a conveyance path of the beef trimmings, a sampling roller 30 disposed above and biased downward towards the conveyor belt so as to contact the beef trimmings during conveyance and bunches of sampling filaments 40 suspended above the conveyor and hanging downwards sufficiently to contact the beef trimmings conveyed along the conveyor belt.

Each of the aforementioned devices includes a sampling member that contacts at least some of the beef trimmings during conveyance along the conveyor belt before collection in the combo bin and attachment features that allows the sampling medium to be attached and positioned within the conveyance system. The devices may include a base portion or plate attachable to the conveyance system and a support component that interfaces with one or more attachment features to support the sampling member within the conveyance system at a sampling position that allows the sampling member to be easily removed and replaced to facilitate sampling of each batch. Additional details of each are provided in FIGS. 2A-4B and described further below.

Figure 2A:
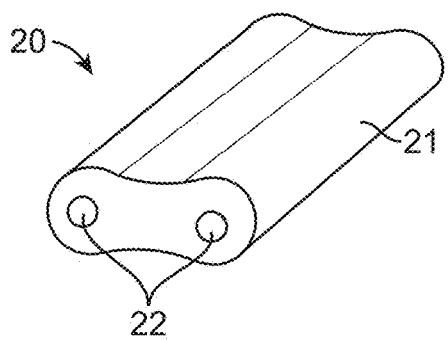
FIGS. 2A-2H are illustrations of example sampling members in accordance with embodiments of the invention.
Figure 2B:
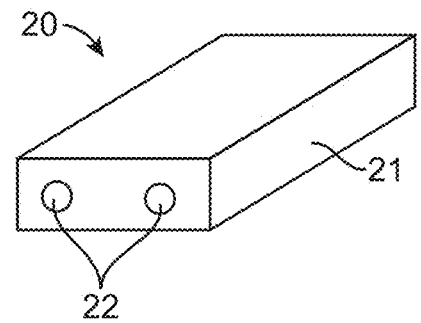
Figure 2C:
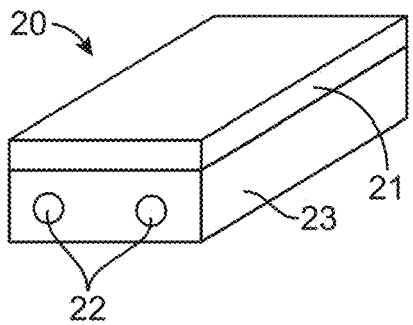
Figure 2D:
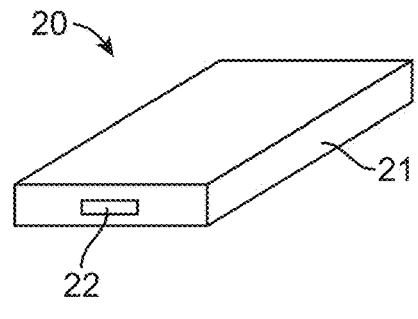
Figure 2E:
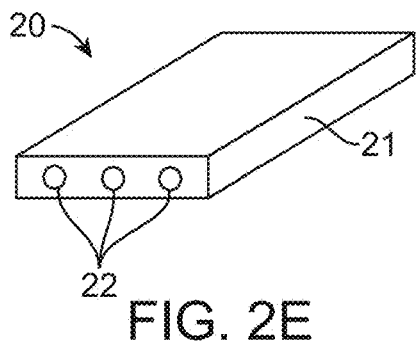
Figure 2F:
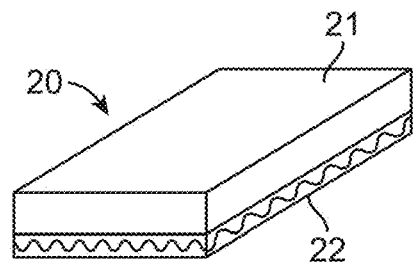
Figure 2G:
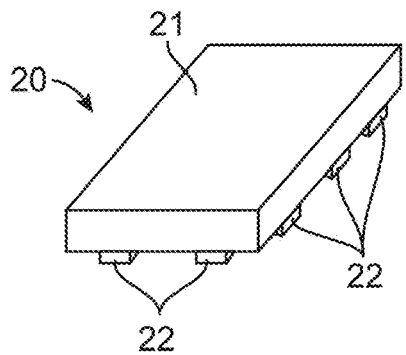
Figure 2H:
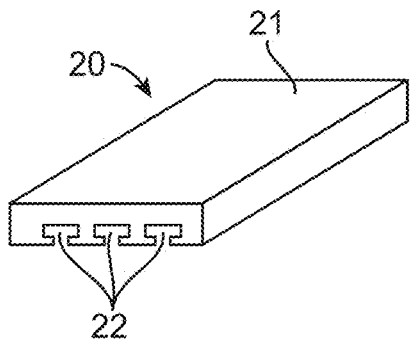

FIGS. 2A-2B illustrate embodiments of the elongate sampling member 20 (associated sampling device and support component not shown). Each of sampling members includes a sampling medium 21 for retaining a liquid or solid residue of the items which the medium contacts and an attachment feature 22 for facilitating attachment of the sampling member to the support component of the sampling device. In each of FIGS. 2A-2H, the sampling medium 21 is an elongated sponge. In these embodiments, the sampling medium is elongate along two axis, its length and width such that one major surface remains facing the items conveyed along the path. In some embodiments, such as that shown in FIG. 2C, the sampling medium 21 may be supported by a substrate 23, which may be constructed of any suitable material. The attachment feature 22 may include one or more passageways extending through the sampling member, such as shown in FIGS. 2A-2E, adapted to interface with corresponding shafts or rods of an associated sampling device. In other embodiments, the attachment feature 22 may include any of an adhesive, snap-fit or interference fit type coupling, or interlocking grooves or protrusions, such as shown in FIGS. 2F, 2G and 2H, respectively. It is understood that in various other embodiments, the sampling member may be without such an attachment feature and may be constrained or maintained in position by one or more various other components interfacing with a base portion or base plate of the sampling device.

Figure 3A:
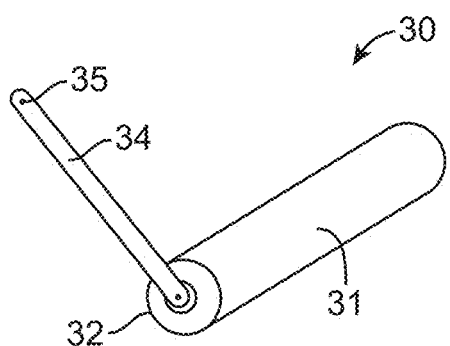
FIGS. 3A-3F are illustrations of example sampling rollers in accordance with embodiments of the invention.
Figure 3B:
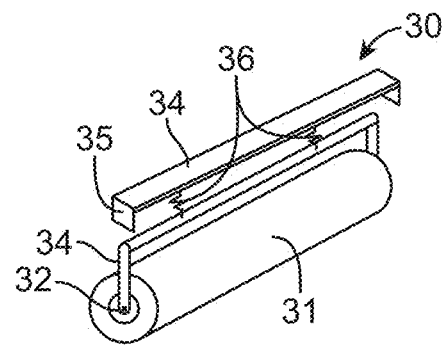
Figure 3C:
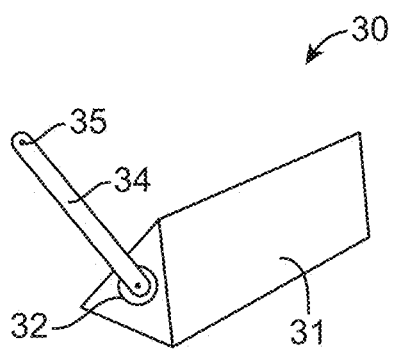
Figure 3D:
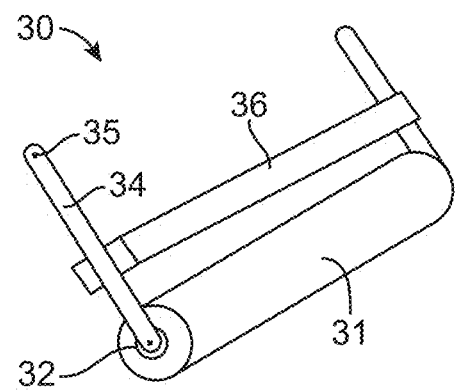
Figure 3E:
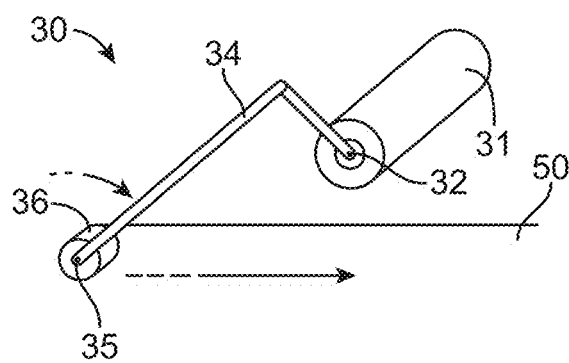
Figure 3F:
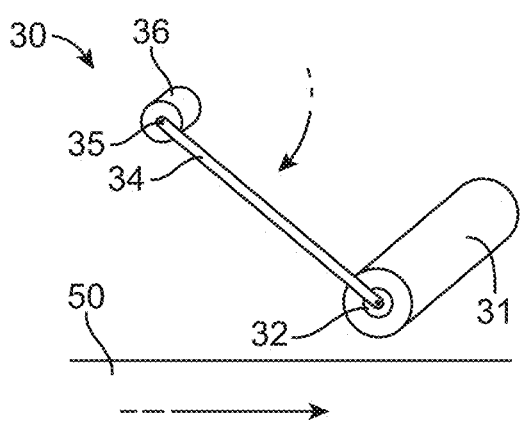

FIGS. 3A-3F illustrate embodiments of the sampling roller 30, which includes the sampling medium 31 in the form of a foam roller or sleeve disposed on a roller substrate, an arm 34 that facilitates attachment of the roller 30 to the conveyance system and an attachment feature 32, a cylindrical passageway, that facilitates attachment of the cylindrical sampling medium 31 to a support component (e.g. roller body) as well as easy removal and replacement by feeding the cylindrical sampling medium onto and off of the roller body. The other end of the arm 34 including a coupling mechanism 35, such as a wing-nut or other screw-type coupling mechanism, for coupling the arm 34 to the conveyance system. While the sampling roller is typically depicted as a cylindrical roller that rolls over the surface of the items being conveyed, it is appreciated that the roller may utilize various other shapes, such as various polygonal shapes or a triangular shape as shown in FIG. 3C. The shape of the sampling roller may be selected according to the application or for a desired roller movement. The arm 34 is configured to support the sampling roller 30 so as to suspend the sampling roller from above the conveyance path. In some embodiments, the arm 34 includes a biasing mechanism 36 that provides a biasing force to press the roller 30 against the items over which the sampling roller 30 rolls so as to improve retention of liquid or solid residue from the items. The biasing mechanism 36 may include linear springs, as shown in FIG. 3B; a weight, as shown in FIG. 3D; or radial springs that may be incorporated into the coupling feature 35, as shown in FIGS. 3E-3F. In some embodiments, the sampling roller may be configured to remain slightly separated from a conveyance surface so as to roll over the batch items transported thereon and sample material only from the batch items so as to avoid contact with the surface of the conveyor belt.

Figure 4A:
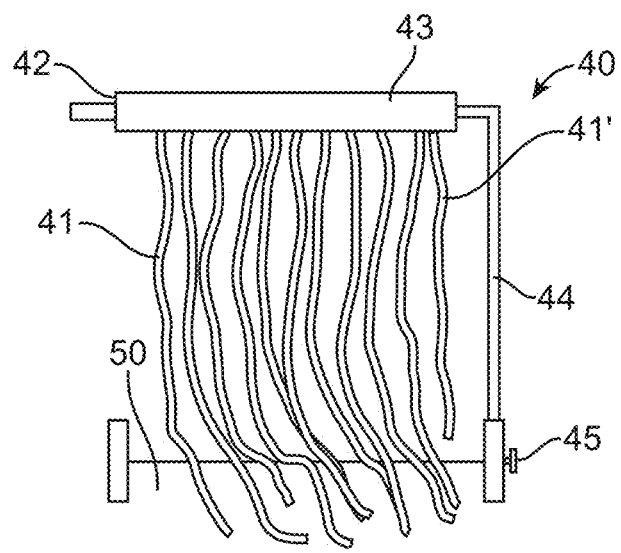
FIGS. 4A-4B are illustrations of example sampling filaments in accordance with embodiments of the invention.
Figure 4B:
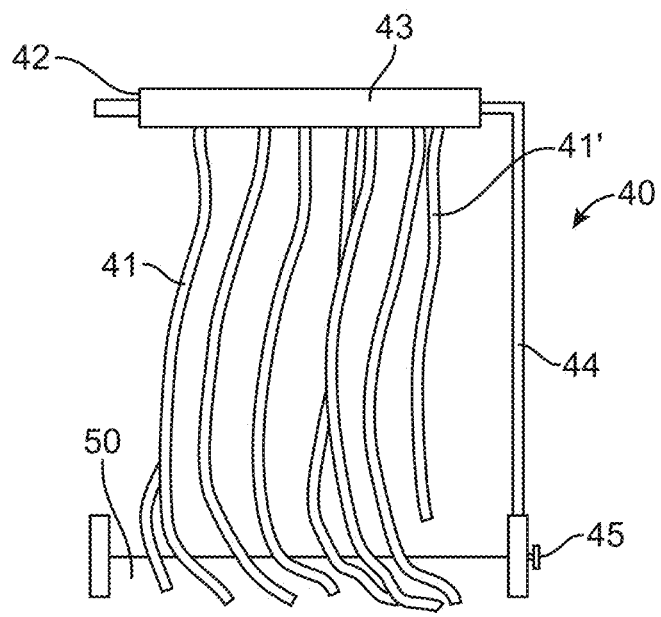

FIGS. 4A-4B illustrate example embodiments of the sampling filament device 40. The sampling medium 41 are filaments extending into the conveyance path, typically flexible absorbent filaments, fibers or yarns, as shown in FIG. 4A, or strips of material, as shown in FIG. 4B. In some embodiments, the sampling filaments are attached to a support member 43 which is releasably attached to the arm 44, which in turn is coupled with the conveyance system by a coupling mechanism 45, such as a wing-nut or other screw-type coupling mechanism. The sampling member support 43 includes an attachment feature 42, such as a passageway, that interfaces with the arm 44 so as to suspend the sampling medium 41 above the conveyance path so that the filaments hang into the conveyance path and contact items being conveyed. It is appreciated that the filaments may be adapted as needed for a particular application. For example, the filaments may be weighted to improve contact between the filaments and items passing therethrough, the filaments may be dragged over the conveying surface 50 so as to lengthen the time of contact, or the filaments may be constructed so as to contact the items being conveyed without contacting the conveying surface by using shorter filaments 41', as shown in FIG. 4B. This configuration may be useful to provide improved sampling of the items being conveyed while avoiding contact and sampling of the conveyor belt surface.

Figure 5A:
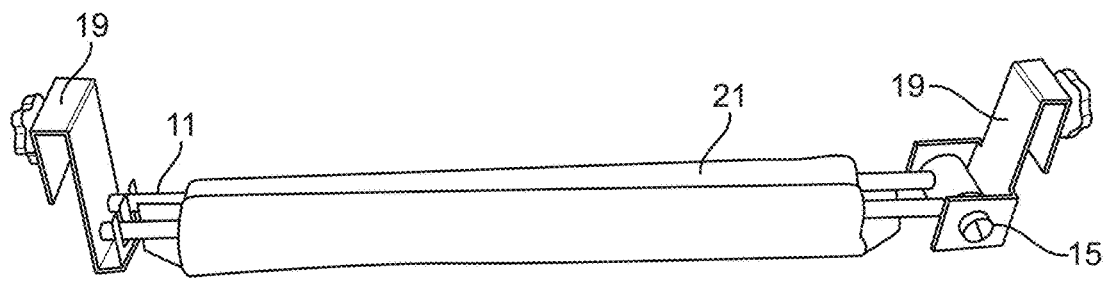
FIGS. 5A-5D illustrate steps of attaching and positioning the front end sampling sponge on the support component of the sampling device.

FIG. 5A illustrate an embodiment of the elongate sampling member 20 device. In this example, the device includes a base member 12 attached to the conveyor belt, a sampling support 11, and an elongate sampling member 20 disposed on the sampling member support 11. In this embodiment, the sampling member support 11 comprises two elongate shafts over which the sampling member 20 (e.g. sponge) is positioned such as by feeding the sampling member 20 over the rods, as shown in FIG. 5C. The dimensions of the elongate shafts correspond to the axial passageways extending through the elongate sampling member. The base portion 12 includes coupling mechanisms 19 on opposite sides for attaching to the conveyance system, the coupling mechanisms 19 may utilize a wing-nut, knob or other screw-type coupling mechanism to affix the base to the front end of the conveyance system. The sampling member support 11 is attached at one end to the base 12 by a pivotal coupling 15 such that the support 11 pivots upwards to allow for easy removal and replacement of the sampling member 20. In some embodiments, the base 12 and sampling member support 11 are constructed from stainless steel, which can be easily sanitized by the same procedure the conveyance belt is sanitized, typically by a sanitizing spray.

Figure 5B:
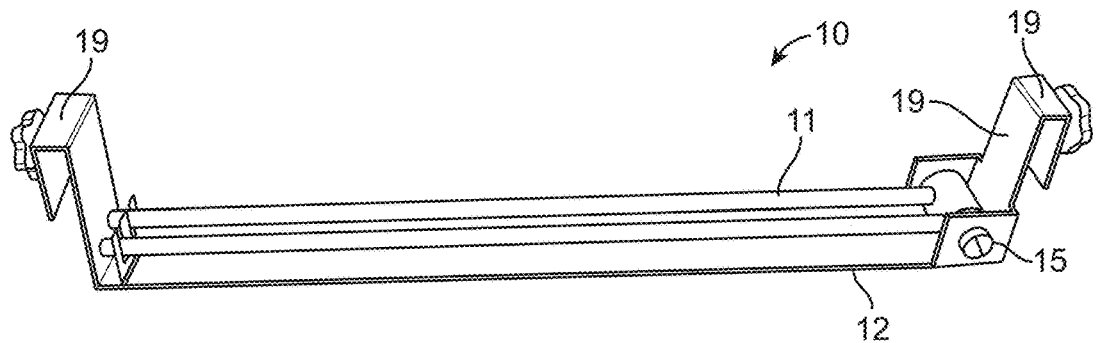
Figure 5C:
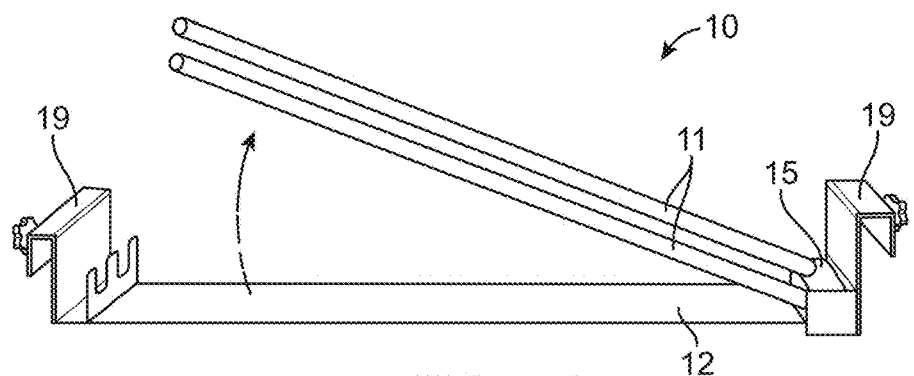
Figure 5D:
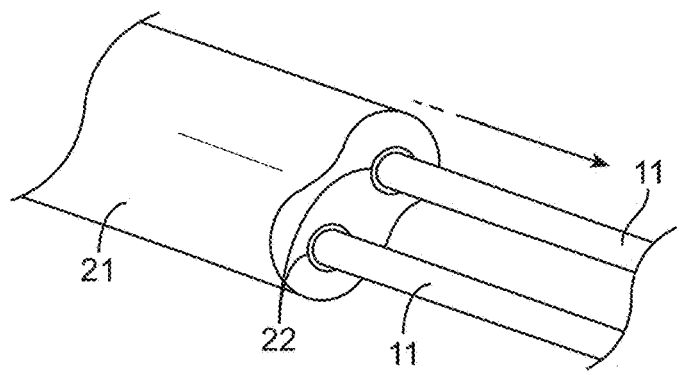

FIGS. 5A-5D illustrate sequential steps in preparing the device for sampling. Once the frame or base of the sampling device body is coupled to the front end of the conveyor belt via coupling mechanisms 19 on opposite sides, such as shown in FIG. 1, the attachment rods are pivoted upwards, as shown in FIG. 5B, and a new sterile front sponge sampling medium 21 is fed onto the rods such that the rods are received into the axial passageways of the attachment features 22. Once the front end sponge member is entirely positioned on the rods, the rods are pivoted downwards and received within a recess or notched holder at the opposite end of the sampling device. The mechanism may rely on gravity to keep the rods in place or may further utilize another coupling mechanism (e.g. snap-fit, lock, lever, etc.) to hold the rods in place. The front end sponge sampling medium 21 is now positioned in the sampling position, as shown in FIG. 1, such that conveying beef trimmings along the conveyor belt passes the beef trimmings over the sponge, which then retains liquid and/or solid residue from the outer surface of the beef trimmings, to allow subsequent testing of the sponge to assess whether the targeted agent is present within the batch of beef trimmings.

Figure 6A:
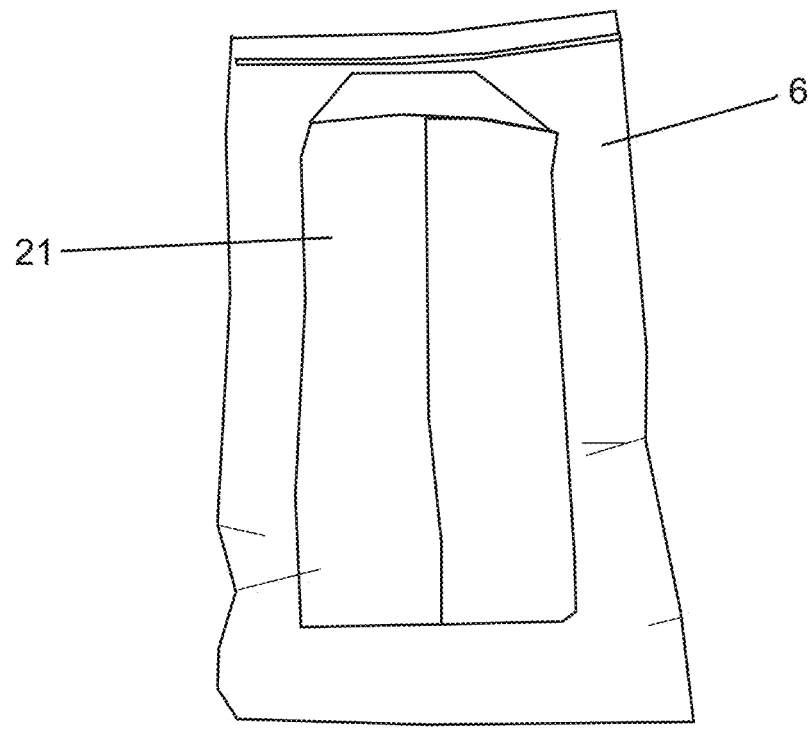
FIGS. 6A-6B illustrate use of the sampling member in culturing for a targeted agent.
Figure 6B:
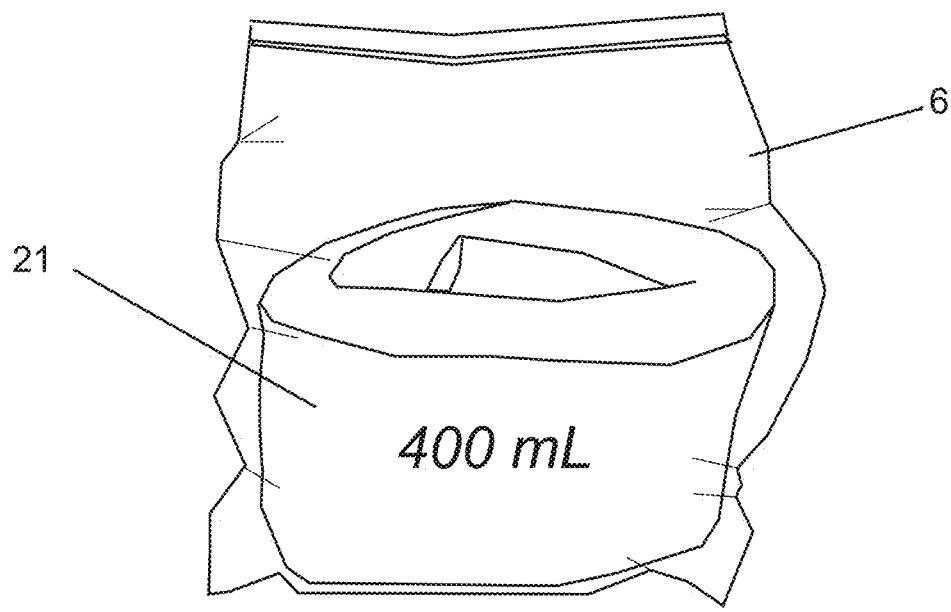
Figure 7A:
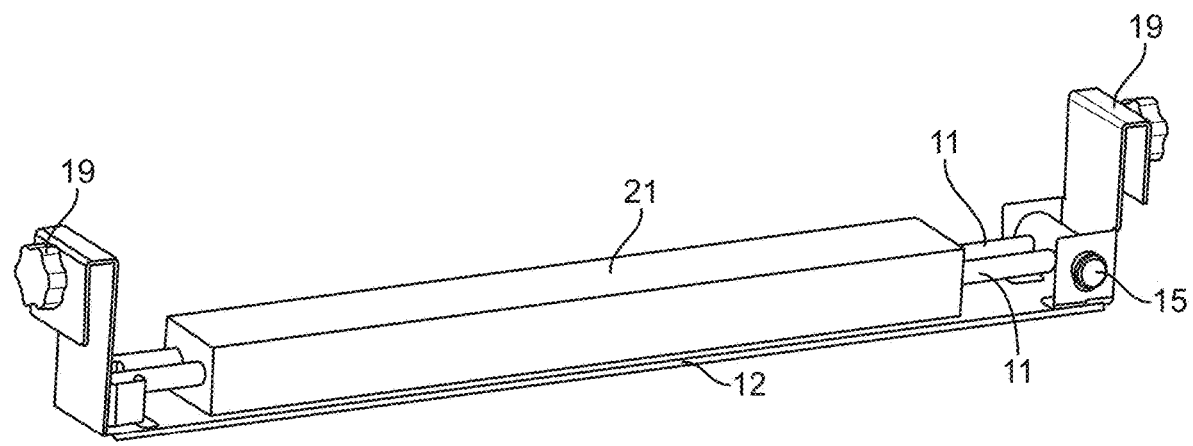
Figure 7B:
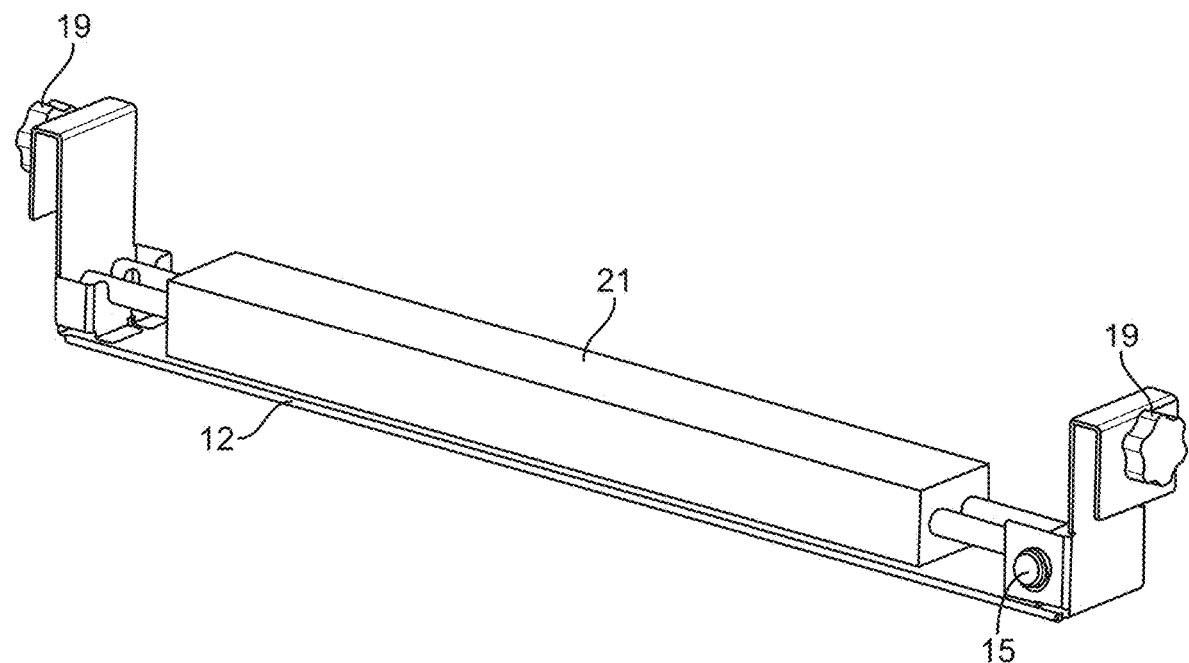

FIGS. 6A-6B illustrates the front sponge sampling medium 21 after exposure to a conveyed batch of beef trimmings, the front sponge sampling member having been folded in thirds and placed within a standard sampling bag 6. The elongate sampling member 20 is maintained within the sampling bag 6 along with a nutrient broth for culturing of the targeted agent. As described in further detail below, the sampling member is maintained along with the nutrient broth within a temperature range and for a duration of time sufficient for incubation of the targeted biological agent. After incubation, if the targeted agent is present, it will have multiplied to sufficient levels to be readily identifiable through various means as would be known to one of skill in the art of biological sampling. Although this process may take considerable time (1-3 days), since each batch is associated with a sample, the batch of beef trimmings can be stored or can be shipped or proceed to another processing facility during such time. Should the testing indicate the presence of the targeted agent, then the identified batch can be intercepted and subsequently discarded or further processed to kill or remove the agent.

FIGS. 7A-7G illustrate views of another sampling device utilizing an elongate sampling member 20, in accordance with embodiments of the invention. In this example, the elongate sampling member 20 comprises a sample medium 21 (e.g. cellulose sponge or foam) that is rectangular in shape. It is appreciated that the elongate sampling member 20 in this or any embodiment described herein may be dimensioned so as to extend across the conveyance path to ensure contact with at least some portion of the batch conveyed. In many embodiments, the sampling members are configured so as to extend substantially across the entire conveyance path so as to contact a majority of the items conveyed in a batch, thereby providing improved sampling coverage of the batch as compared to conventional sampling methods. For example, when used with a conventional conveyor belt, the front end sampling member may be configured so as to extend substantially across the front end of the conveyor belt. In certain embodiments, the front end sponge member is substantially rectangular having a length between 6 inches and 36 inches, a width between 0.5 inches and 12 inches, and a thickness between 0.1 inch to 6 inches, preferably the rectangular sponge is about 24 inches in length, about 4-6 inches in width, and about 1-3 inches in thickness. These dimensions are advantageous in providing a large enough surface to contact a substantial portion of the batch during conveyance as well as enough sampling medium to absorb a sufficient amount of residue from the conveyed batch items to be representative of the entire batch. In addition, these dimensions and construction allow the sampling sponge member to be easily folded and contained within a standard sized biological sampling bag. This is particularly advantageous over current industry methods using destructive testing of relatively large cuts of beef or meat, since sampling often requires cutting or mutilating the trimmings to allow the sample to fit within a standard sized sampling bag. This conventional approach is not only time consuming, but considerably increases the complexity, costs and risks of cross-contamination. Thus, the sampling devices and methods described herein provide improved coverage of the entire batch, while improving cost, ease and efficiency in sampling and avoiding unnecessary destruction of non-contaminated product.

In some embodiments that specifically address the need for sanitary design and GMP compliance, the prepared sampling device includes three parts. It includes a base plate folded or formed to allow fastening in the product stream, a support plate to hold the sampling member and the sampling member. Examples of these embodiments are shown in FIG. 10A-10D. The folded portions of the base plate that allow mounting in the product stream can also include also include a slit and "t" cut hole designed for a lock and key fit of the support plate. The end of this second plate is slid into the slot of the mounted plate and a narrow portion enters the "t" cut hole. By sliding this second plate forward, a wider portion locks the second plate in place without the need for additional small metal parts or fasteners that might become foreign object contaminants in the product stream. Other lock and key configurations are also possible. This second plate supports that sampling member as discussed in the next paragraph.

In one aspect, such as in the embodiment of FIG. 5A-5D, the sampling member of the sampling devices is constructed from foam and fusible fabric. The sampling member has no hard parts such as rigid metal or plastic parts. The foam is soft and resilient and the fabric is porous, soft and durable. The two materials may be sewn together so that the resulting sampling member provides the advantageous properties of each material. The sponge is provided in a plastic bag and together can be sterilized using Ethylene oxide or other suitable sterilization methods. The plastic bag is sufficiently strong and constructed such that it may also be used directly for culturing the sponge sample after use for batch sampling. The sampling member may be constructed without any hard or rigid components so that bacteria can easily be released from the sampling member and suspended into a culture broth using a regular stomacher or by kneading manually, without damaging the plastic bag. The size and thickness of the sampling member should be large enough to sample and small enough for easy handling in microbiology testing. In the example shown in FIG. 5A, the sampling member is about 16 inches long, 4 inches wide and ½ inch thick. In another embodiment shown in FIG. 7A, the sampling member is about 24 inches long, 4 inches wide and ½ inch thick. It is appreciated that the sampling member and associated support and base plates may be dimensioned in various sizes as needed for a particular conveyance system. In another aspect, the sampling member is flexible enough so that it can be folded in half or in thirds-width-wise and placed in a standard sized Whirl-Pak. In accordance with some methods, the sampling member can be removed from the sampling rods in a rolling motion that simultaneously coils or folds the sponge and then placed directly into the bag for culturing. A suitable amount of culture broth is added, typically about 400 mL of culture broth or enough broth to soak the sponge. Such an amount is adequate for kneading or stomaching the sample bag and leave sufficient room for incubation.

In another aspect, the elongate sampling member 20 is a die cut cellulose sponge. It is appreciated that a cellulose sponge may be used as a sampling medium in any of the sampling device embodiments described herein. A sampling medium free from all biocides is particularly useful for sampling microorganisms but must be handled aseptically or maintained in a dry state since moisture may result in mold growth. Many of the above attributes described with respect to the foam sampling member are also applicable to a sampling member formed of cellulose sponge material. In addition, the cellulose sponge has additional advantages over foam in that the cellulose sponge is provided in a compressed form, typically less than 15 mm thick. In this compressed form, the cellulose sponge member also exhibits stiffness greater than that of foam such that the sampling member can be more easily fed over the sampling member support 11. Typically, after positioning the sampling member comprising compressed cellulose sheet material on the sampling member support, the sampling member is hydrated by sterile water, either before or after securing the sampling member to the base portion attached to the conveyance system.

The sampling medium (e.g. cellulose sponge) can be fastened to the support plate in a variety of manners including those previously discussed. In a particularly useful embodiment, the sampling member can be die cut while in a compressed dried state such that it dimensionally matches the second plate for length and width. It is possible to die cut the sponge in its expanded form but this requires that sponge either be redried or treated and packaged immediately to prevent mold growth. During this die cutting process pairs of small slits are cut out to allow the second plate to be weaved through the sponge. By spacing the pairs of slits along the length, most of the sampling medium will be exposed to the product stream with only small portion wrapping around the back side of the second plate.

Although not necessary for practicing the art, it is easier to handle such manipulations while the sponge is dried and compressed. In those embodiments where microorganisms are being sampled and where a cellulose sponge is being used, it is useful to swell the compressed die cut sponge and package the sponge in a resealable package suitable for sterilization or pasteurization as needed for the application. Chemical and irradiation techniques are both useful for this purpose.

Figure 8A:
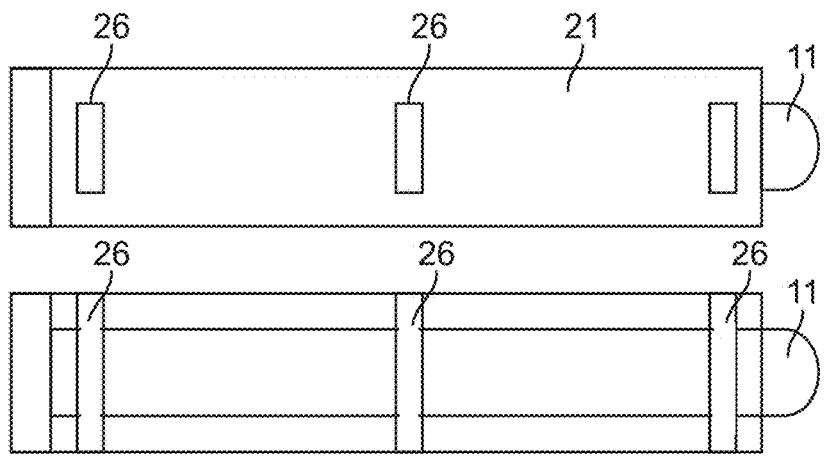
FIGS. 8A-8D illustrate views of example sampling members in accordance with embodiments of the invention.
Figure 8B:
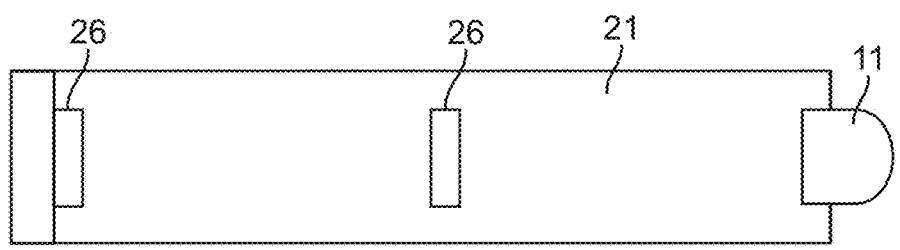
Figure 8C:
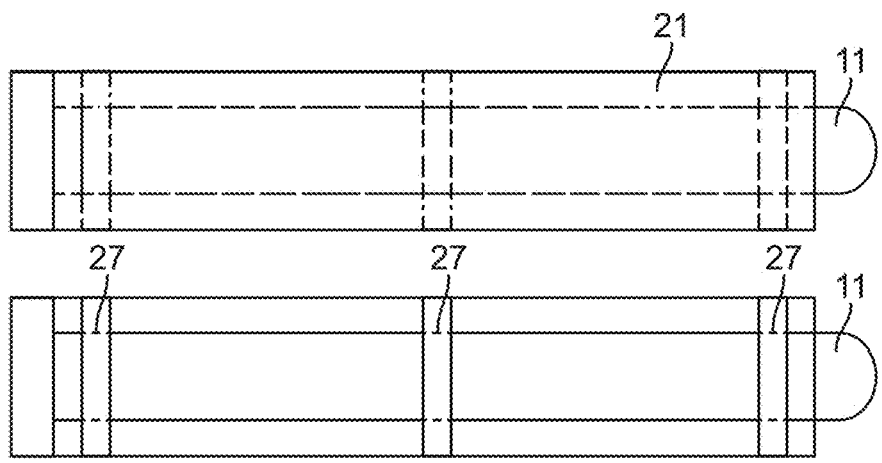
Figure 8D:
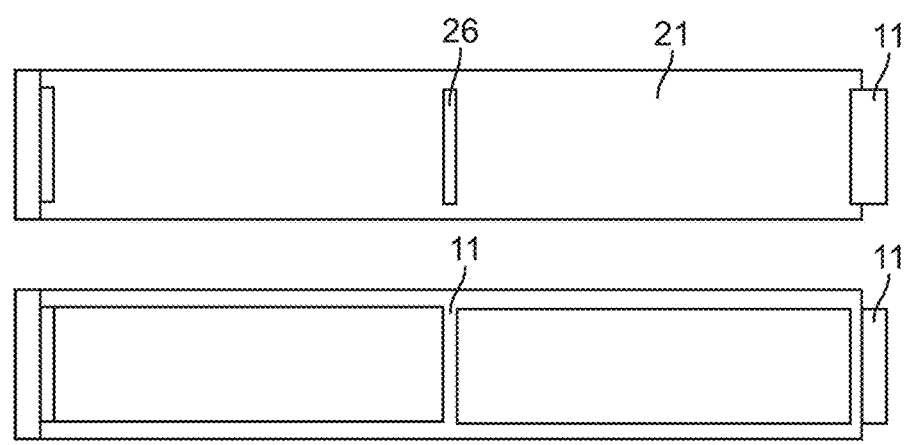

An example of the sample medium configurations described above are shown in FIGS. 8A and 8B. FIG. 8A shows a top view (T) and bottom view (B) of a cellulose sponge sampling medium 21 having pairs of small slits 26 that allow the support plate 11 to weave through the slits along the length of the sampling medium 21. As can be seen in the top view (T), only small portions of the metal support plate 11 are visible at three discrete locations along the sponge. FIG. 8B shows a top view (T) of an alternative embodiment having a pair of slits in the middle and one slit near each end, so as to minimize the exposure of the metal plate 11 on the top side where the product is sampled. In another example, one could achieve a similar configuration of the sampling member as described above by attaching short strips 27 width-wise on the backside of the sampling member. The strips could be secured to the sampling member by sutures, adhesive or other suitable means of attachment. An example of this configuration is shown in FIG. 8C. As shown in the bottom view (B), the strips 27 extend along the back side of the sampling member 20 such that the support plate 11 can be easily inserted through the loops defined in part by the strips 27. This is advantageous as it allows substantially the entire top surface of the sampling medium 21 to be exposed to the product stream, as can be seen in the top view (T). FIG. 8D shows yet another embodiment in which a frame 16 is used which includes a cross piece that spans across the sampling medium such that a majority of the top surface of the sampling member is exposed to the product stream.

Figure 9A:
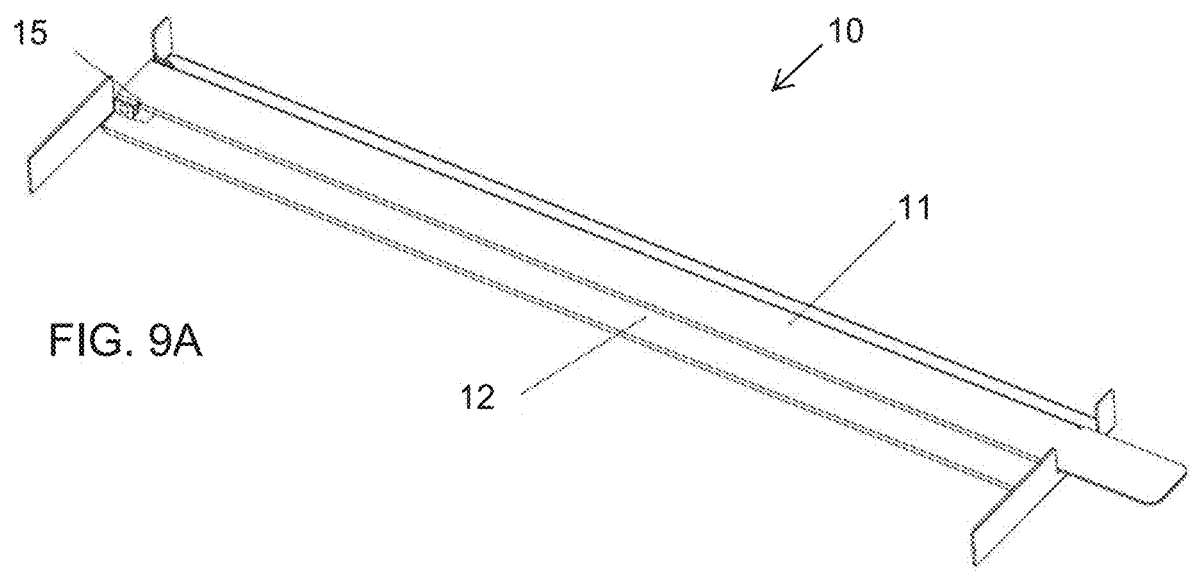
FIGS. 9A-9B illustrate an example sampling device in accordance with embodiments of the invention.
Figure 9B:
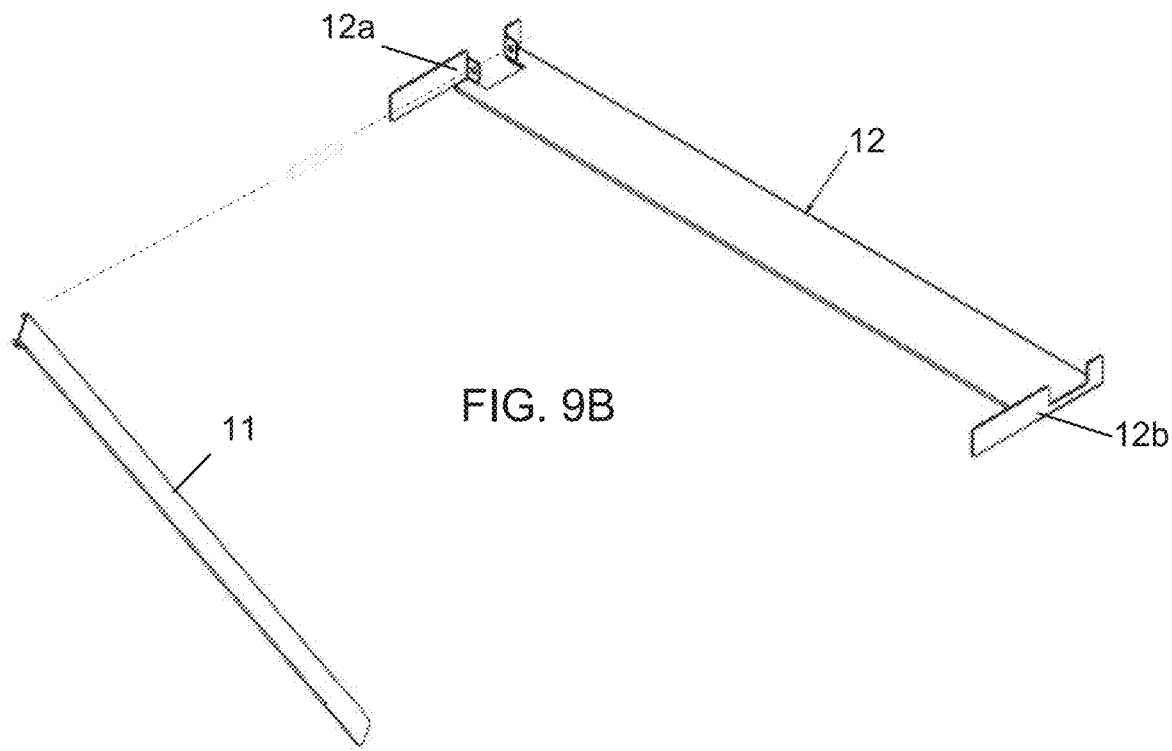

FIG. 9A illustrates another example embodiment of a sampling device 10 for use with a sampling member (not shown). An exploded view is shown in FIG. 9B. This embodiment includes a sampling member support 11 shaped as a rectangular plate that is attached at one end to a rectangular base plate at a pivotal coupling 15. Opposing ends 12a, 12b of the base plate 12 are folded so as to extend laterally outward at a substantially perpendicular angle. Each end includes a cut-out notch for receiving the sampling member 12. The folded end portions also function to attach the base plate to the conveyance system in a number of ways. For example, the end user may modify a portion of the folded end portions as needed by machining a hole or notches to interface with corresponding features on the sides of the conveyance system or the folded end portions may simply be clamped to side walls of the conveyance system.

Figure 10A:
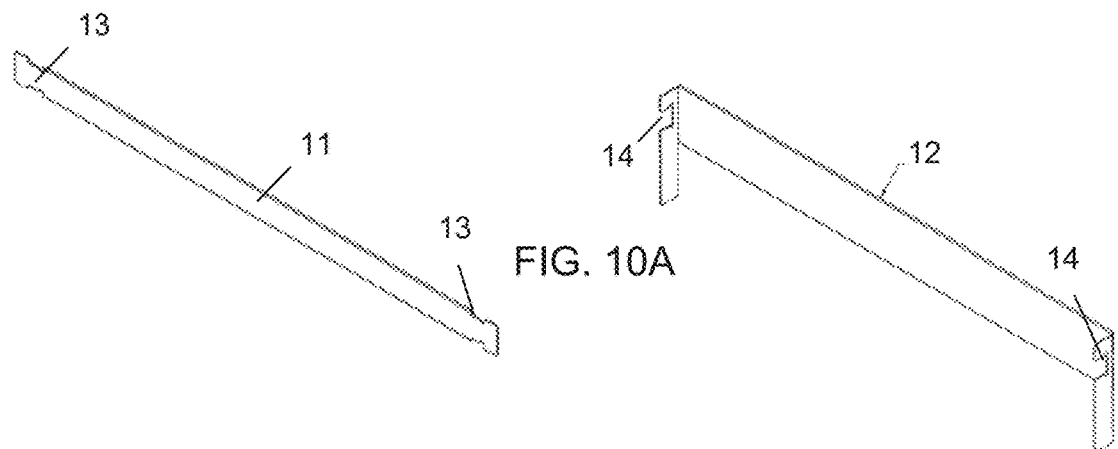
FIGS. 10A-10D illustrate example sampling devices in accordance with embodiments of the invention.
Figure 10B:
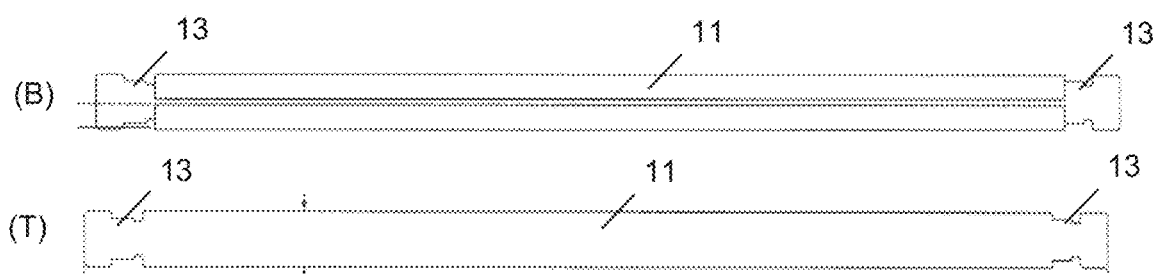
Figure 10C:
Figure 10D:
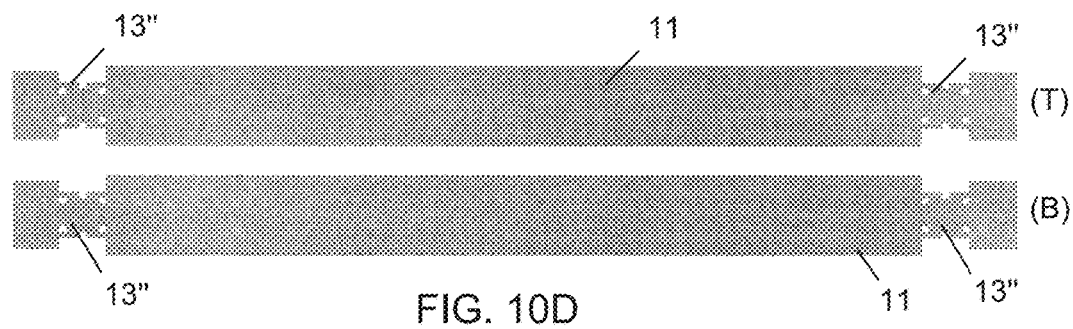
Figure 10D:
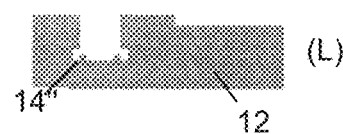

FIGS. 10A-10D depicts a sample member device for releasably securing an elongate sampling member 20, such as any of those described herein, within a product stream. This embodiment includes an elongate base plate 12 for attaching to the conveyance system and a sampling member support plate 11 releasably attachable to the base plate 12 and on which the elongate sampling member can be releasably mounted. The sampling member support plate can be releasably secured to the base plate 12 by interfacing with one or more engineered attachment regions 13 near opposing end portions of the support plate with corresponding engineered attachment regions 14 on the folded portions near opposing ends of the base plate 12. The coupling features 13 may be engineered regions, such as may be formed by folding, cutting or welding in various shapes or to include slots or openings, that interface with corresponding shapes or protrusions in the base plate so as to secure the sampling member support plate 11 in the sampling position in the conveyance stream. As shown in the example of FIGS. 10A and 10B, the attachment regions 13 have been engineered to have a stepped-down or cut-out region near each opposed end portions, each stepped-down portion having first and second areas of reduced with, the first being of a smaller width than the second. The cut-out region is dimensioned so as to receive the stepped-down portion and secure the sampling member upon sliding of the sampling member disposed therein in a lengthwise direction. In one aspect, the cut-out is dimensioned in a "t" shape, the width of the lower portion of the "t" corresponding to the width of the first portion to allow placement of the sampling member in the cut-out and the length of the upper portion of the "t" shape corresponding to a width of the second area of the stepped-down portion. FIG. 10B shows top (T) and bottom (B) views of the sampling member in FIG. 10A. In some aspects, the sampling member shape may be dimensioned by folding over of the lengthwise edges of the sampling member to form the desired width-wise dimensions, as can be understood by referring to the bottom view of FIG. 10B. FIG. 10D illustrates views of another example of a sample member device utilizing engineered regions in each of the sampling member support plate and base plates to define corresponding coupling features for securing the support plate to the base plate. FIG. 10D shows top (T) and bottom (B) views of the sample member device in which the coupling features 13" includes multiple holes that receive protrusions of the corresponding coupling feature 14", as shown in FIG. 10D.

Figure 11A:
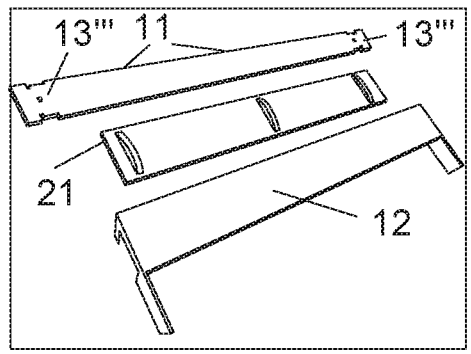
FIGS. 11A-11H illustrate method steps of mounting a sampling member to the sampling device in FIG. 10A.

FIGS. 11A-11H illustrate an example sampling device utilizing an elongate sampling member and method of assembly in accordance with embodiments of the invention. As shown in FIG. 11A, the example sampling device has three components: a docking base 12 with two arms 12a,12b that can be attached to a conveyer, a removable support plate 11 for holding a sampling pad, and a sampling member 20 comprising a compressed, dry cellulose sponge that is to be hydrated after assembling. The back of the sponge sampling member 20 has three belts 27 that hold the sampling member 20 to the support plate 11.

Figure 11B:
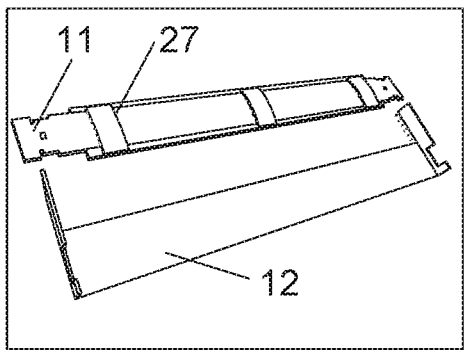
Figure 11C:
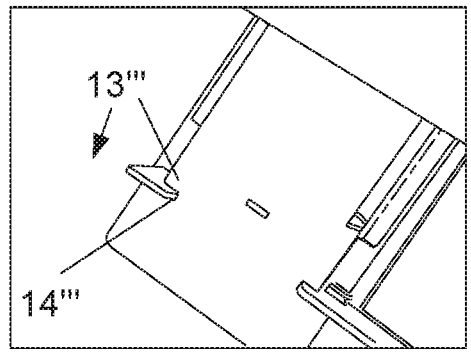
Figure 11D:
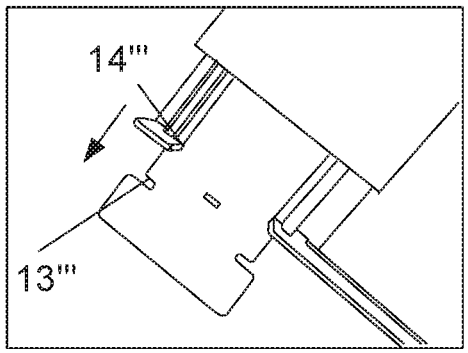
Figure 11E:
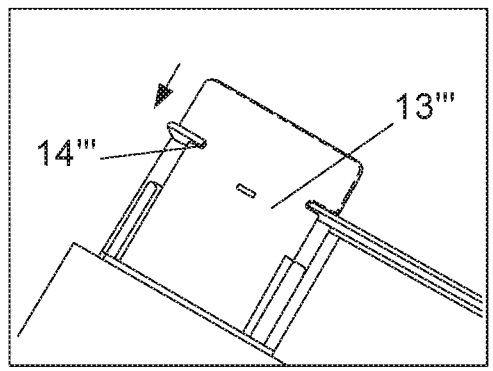
Figure 11F:
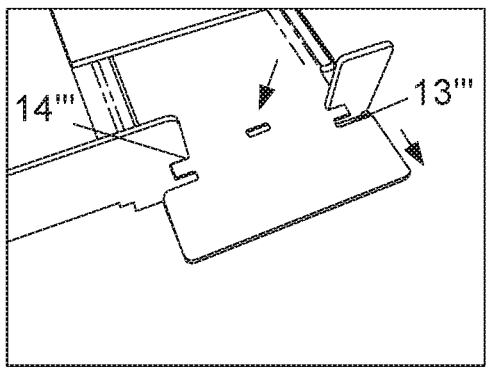
Figure 11G:
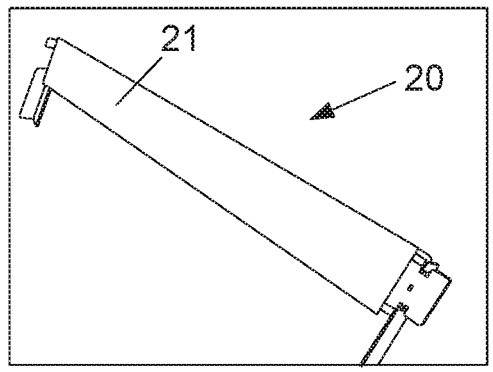
Figure 11H:
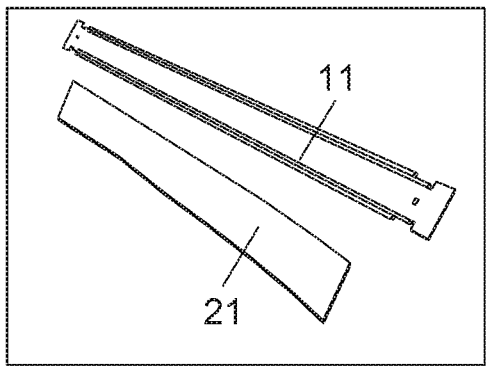

To assemble the sampling member within a sampling device having a removable sample member support plate, such as that shown in FIG. 11A, a user first assembles the sampling member 20 having the sampling medium 21 to the support plate 11 by sliding the plate in between the holding belts 27 and the sampling member 20 so that the sampling member 20 is mounted on the sampling member support plate 11, as shown in FIG. 11B. With the sampling surface side of the pad up, the user aligns the stepped-down portion coupling feature 13''' of the sampling member support plate 11 with the corresponding cut-out coupling feature 14''' of the base plate and pushes the support plate downward into the cut-out, as shown in FIG. 11C. The user then slides the support plate 11 outward until the folded side arm of the base 12 abuts against the end of the stepped-down portion, as shown in FIG. 11D. Next, the user can align and push down the opposite end of the support plate 11 into the t-shaped cut-out in the laterally extending side-arm of the base plate 12, as shown in FIG. 11E. The user then slides the support plate 11 back to allow the small rectangular opening of the engineered coupling feature 13''' of the support plate to align with a small locking bump on base, as shown in FIG. 11F, which helps in securing the support plate to the base plate 12 in the sampling position. After the sampling member 20 is secured into the sampling position in the assembled sampling device, as described above, the sampling medium of the sampling member is hydrated. Sterile de-ironized water (about 200 mL or more) is poured or sprayed evenly onto the sampling member causing the cellulose material to expand instantly so as to be ready for sampling, as shown in FIG. 11G. After a batch of product has been conveyed across the sampling member 20 secured in the sampling device, the device is disassembled to allow removal of the sampling member 20 for testing. In the embodiment of FIG. 11A, the device is disassembled by lifting one end of the plate slightly, sliding the support plate 11 all the way to the other end, lifting slightly and retracting the end out of the cut-out in the folded arm portion of the base 12. The other end is then slid to the open cut-outs of the coupling feature 13''' such that the support plate 11 can be lifted out of the "t" shaped cut-out coupling feature 14''' of the base 12 and the sampling member having the sampling medium 21 removed from the support plate 11, as shown in FIG. 11H. The sampling medium 21 can then be folded and placed into a sample bag for later testing.

Figure 12C:
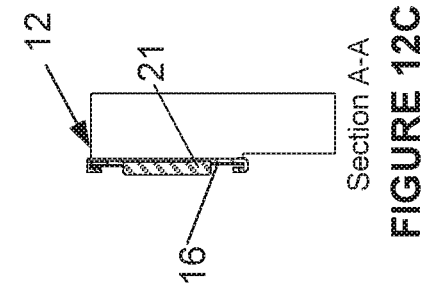
FIGS. 12A-12C illustrate an example sampling device in accordance with embodiments of the invention.
Figure 12A:
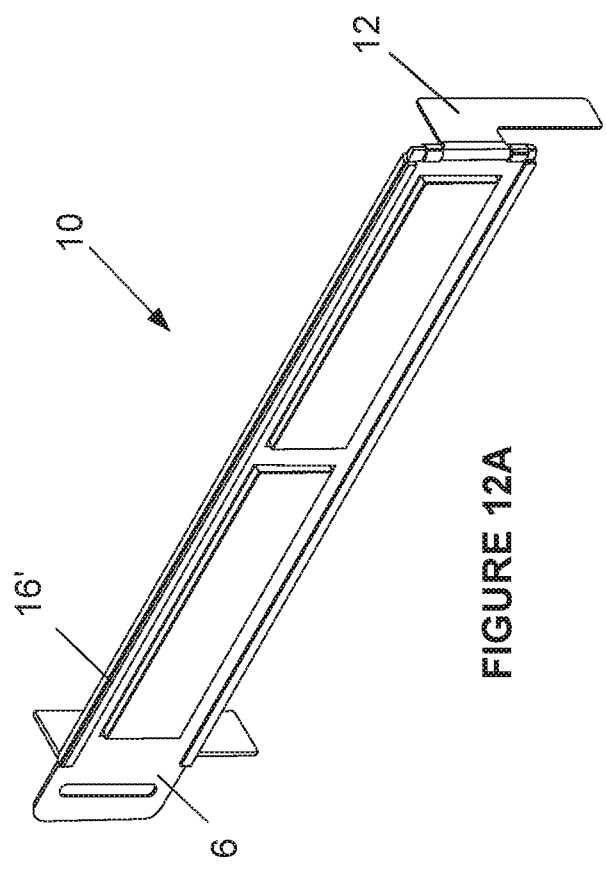
Figure 12B:
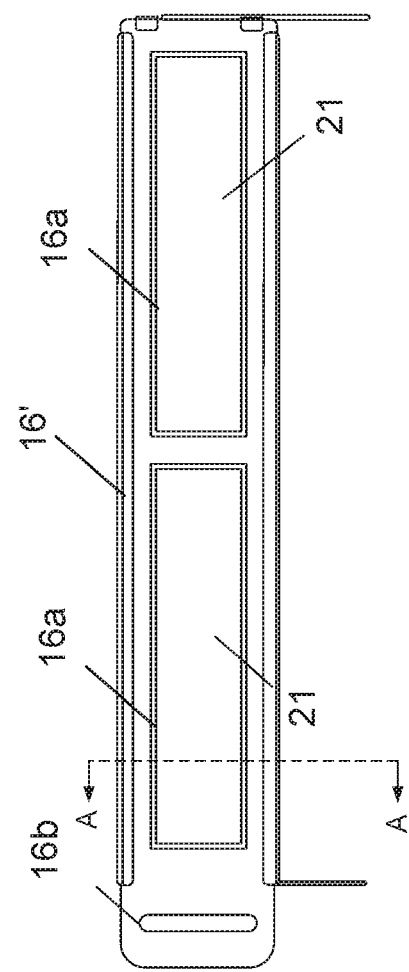

FIGS. 12A-12C illustrate another sampling device 10 for use with an elongate sampling member 20 in accordance with aspects of the invention. In this embodiment, the device comprises a base 12 with a channel formed therein, a removable frame 16, and the sampling member having the sampling medium 21. The sampling member having the sampling medium 21 is inserted into the channel of the base 12 until it abuts against a distal end of the channel and the frame 16 is inserted into the channel over the sampling member having the sampling medium 21. The frame secures the sampling member having the sampling medium 21 within the channel and includes one or more windows 16a through which a majority of the sampling member having the sampling medium 21 is exposed during sampling. The base includes an upper lip 16' extending lengthwise along the top of the channel, which constrains the frame and associated sampling member within the channel. As shown in FIG. 12C, after the sampling member having the sampling medium 21 comprising a cellulose sponge material is hydrated, the sampling member having the sampling medium 21 expands in thickness such that the sampling member protrudes through the windows 16a above the frame of the device during sampling. In one aspect, the frame includes a proximal handle adapted to allow a user to readily insert the device and to facilitate removal of the hydrated sponge upon retraction of the frame by the user. The handles may include a finger slot to facilitate insertion and retraction of the frame.

Figure 13C:
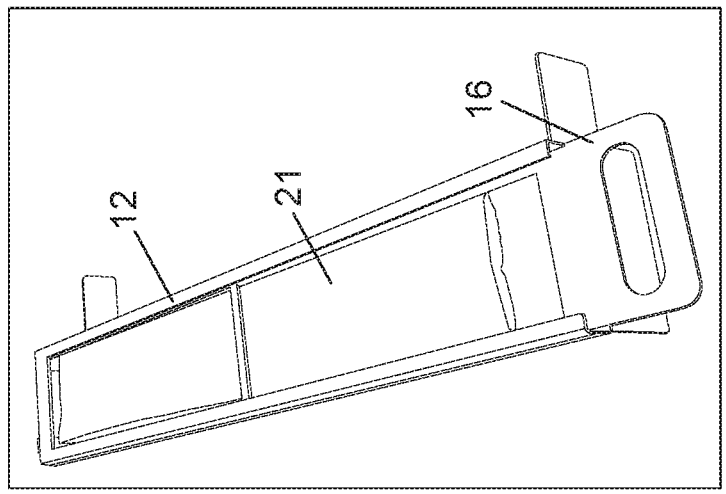
FIGS. 13A-13C illustrate steps of mounting the sampling member to the sampling device in FIG. 12A.
Figure 13B:
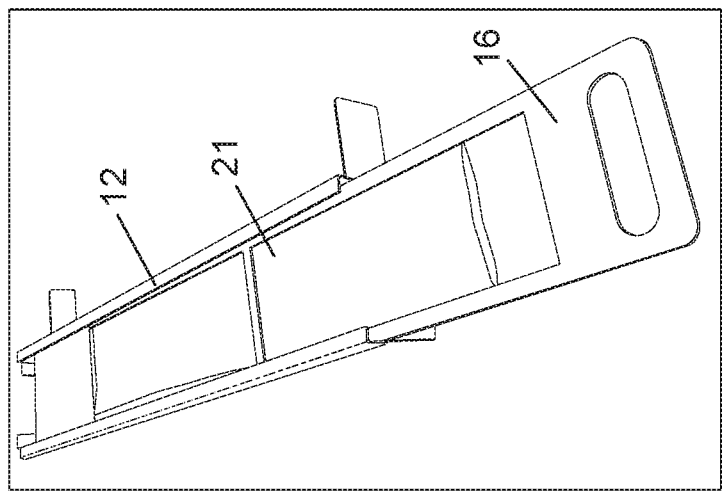
Figure 13A:
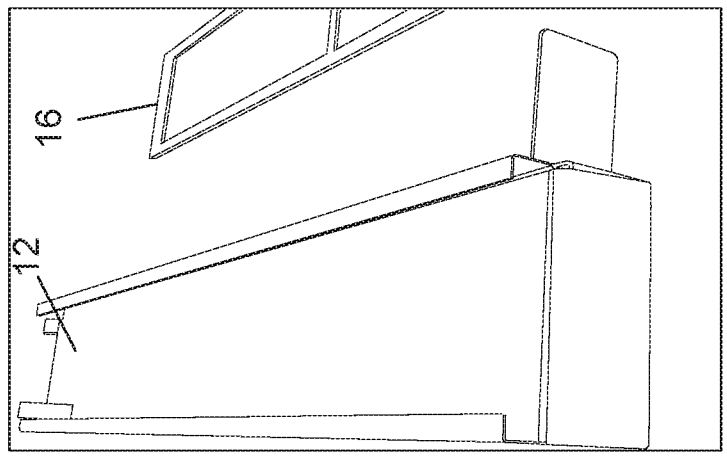
Figure 14B:
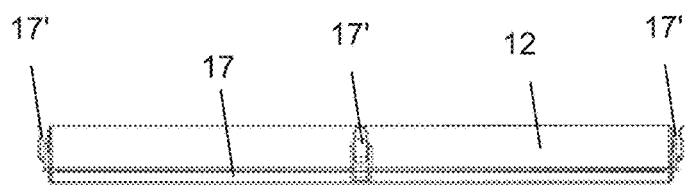
FIGS. 14A-14D illustrate an example sampling device in accordance with embodiments of the invention.
Figure 14A:
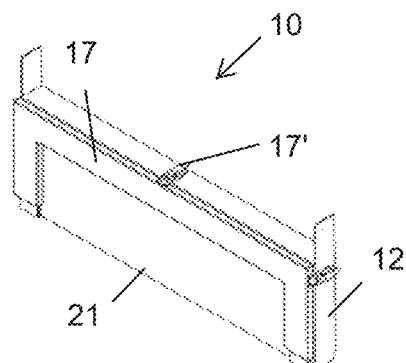
Figure 14C:
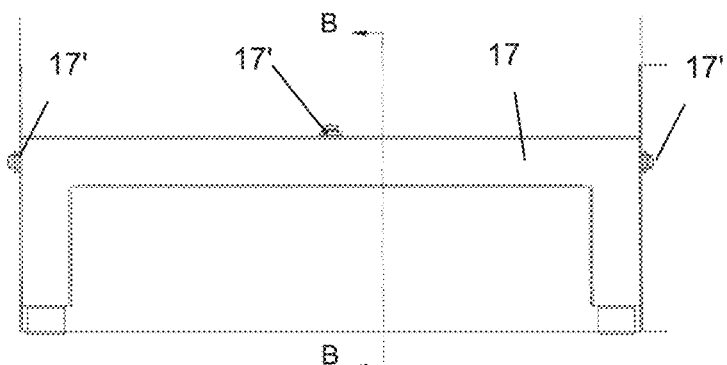
Figure 14D:
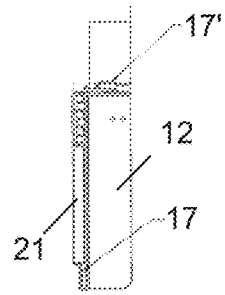

FIGS. 13A-13C illustrate assembly of the sampling device 10 of FIG. 12A. FIG. 13A shows the base plate 12 and insertable frame 16. The sampling member 20 comprising the sampling medium 21 (e.g. sponge material) is inserted into a channel of the base plate 12 until it abuts against a distal edge or tab in the channel and the frame 16 is slid over the sampling member 20. The frame 16 further secures and constrains the sampling member 20 into the sampling position within the channel of the base 12 and may further facilitate insertion and removal of the sponge after sampling. The frame is particularly useful for removing the sampling member comprising a sponge, since after sampling the sponge is hydrated and may be more difficult to remove. The frame 16 may include a proximal handle or finger opening to facilitate manual insertion and retraction of the frame 16 from the channel of the base 12.

FIGS. 14A-14D illustrate another sampling device 10 for use with an elongate sampling member 20 in accordance with aspects of the invention. In this embodiment, the device 10 includes a base 12, an overlay frame 17 and the sampling member 21. The sampling member can be placed within an open cavity of the base 12 and the overlay frame 17 is positioned over the sampling member 21 so as to overlap with one or more edges, typically a lengthwise edge, of the sampling member within the cavity. The frame can be secured to the device with one or more latches 17', thereby securing the sampling member in the sampling position in the conveyance path for sampling.

Figure 15A:
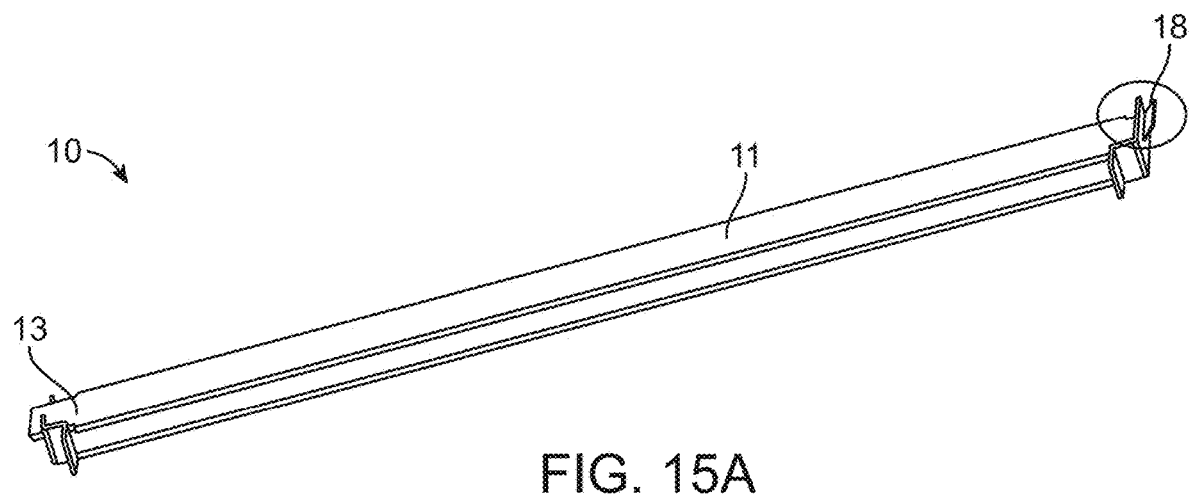
FIGS. 15A-16B illustrate an example sampling device having an detachable hinge in accordance with embodiments of the invention.
Figure 15B:
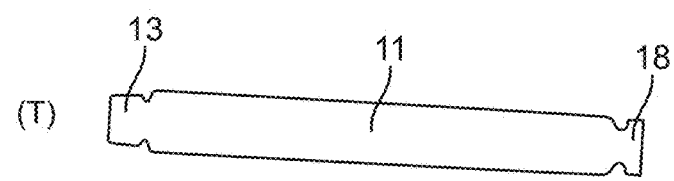
Figure 15C:
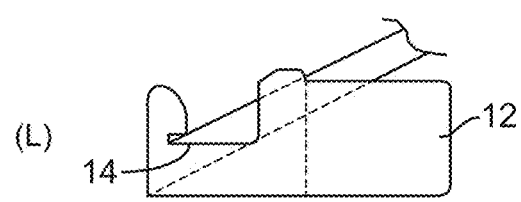
Figure 15D:
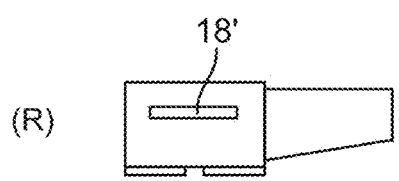
Figure 16A:
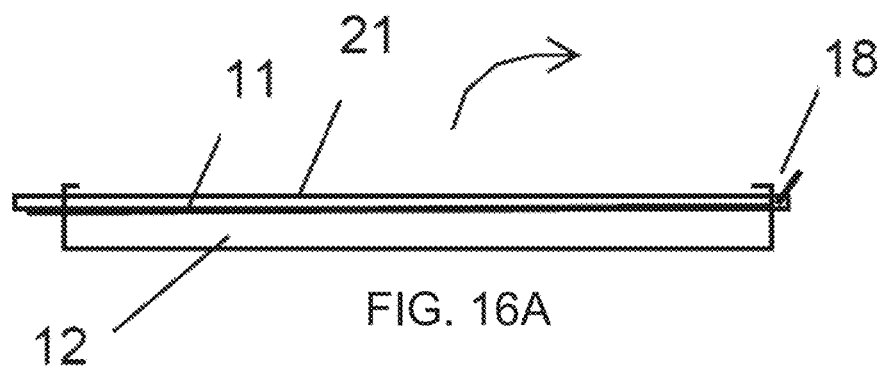
Figure 16B:
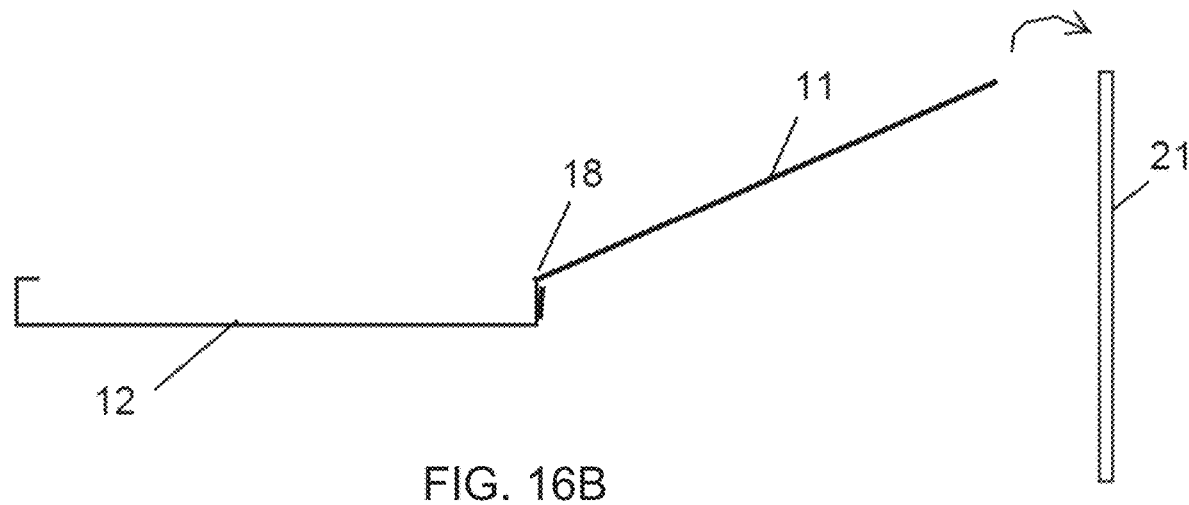

FIGS. 15A-15D illustrate yet another sampling device 10 for use with an elongate sampling member 20 in accordance with aspects of the invention. In this embodiment, the sample member support plate 11 is movably attached to the base plate 12 by a detachable hinge 18. In one aspect, the detachable hinge is defined by a bent tab 18 of an end portion of the support plate 11 that interfaces with a slot 18' of the folded side arm of the base 12. As shown in FIG. 15A, when the sampling member support plate 11 is secured in the sampling position within the base 12, the tab of the hinge is bent upwards. The sampling member support plate 11 can be seen in FIG. 15B. At one end of the support plate 11 is a coupling feature 13 adapted to engage with an corresponding coupling feature 14—an "L" shaped slot in a laterally extending end portion of the base 12 (as shown in the left side view (L)), while at the other end is the upwardly bent tab 18 dimensioned for insertion through a corresponding slot 18' in the opposite laterally extending end portion of the base 12 (as shown in the right side view (R)) thereby allowing the pivoting movement of the sampling support plate 11 shown in FIGS. 16A-16B. In one aspect, the engagement of coupling features 13 and 14 may be similar to that in the above described embodiments. For example, the detachable hinge interface between upwardly bent tab 18 and slot 18' allows for slight movement of the support plate 11 in a lengthwise direction such that the support plate 11 can be secured to the base with the coupling features 13, 14 at the opposite end in a similar manner as that described above in FIGS. 11C-11F.

In one aspect, the upward bent of the tab engages the slot so as to substantially maintain the tab of the support plate 11 within the slot 18' as the support plate is pivoted upwards to facilitate mounting and/or removal of the sampling member 20 from the support plate 11. The upward bent of the tab also allows the support plate 11 to be pivoted beyond 90 degrees to allow easier access to the free end of the support plate 11 so that the sample member 20 can be slid over the support plate 11 before sampling or slid off the support plate 11 after sampling. This configuration is advantageous for applications where the support plate 11 might otherwise be difficult to access due to an elevated conveyance path that might require a user to reach above their head or to use a platform to access.

Figure 17:
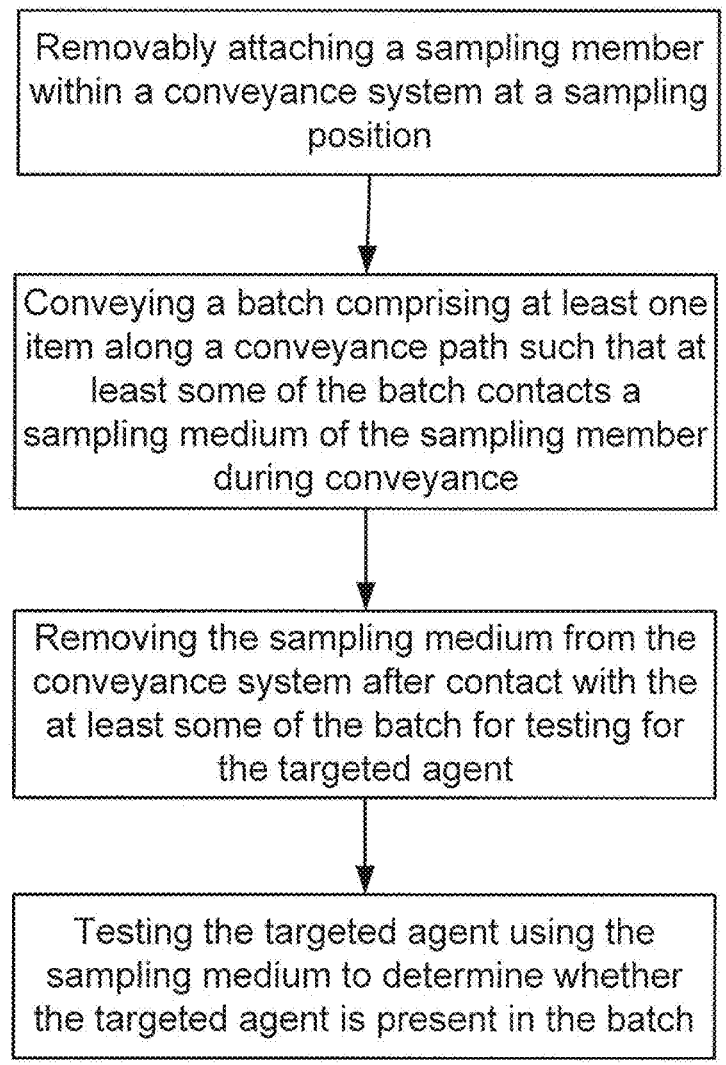
Figure 18:
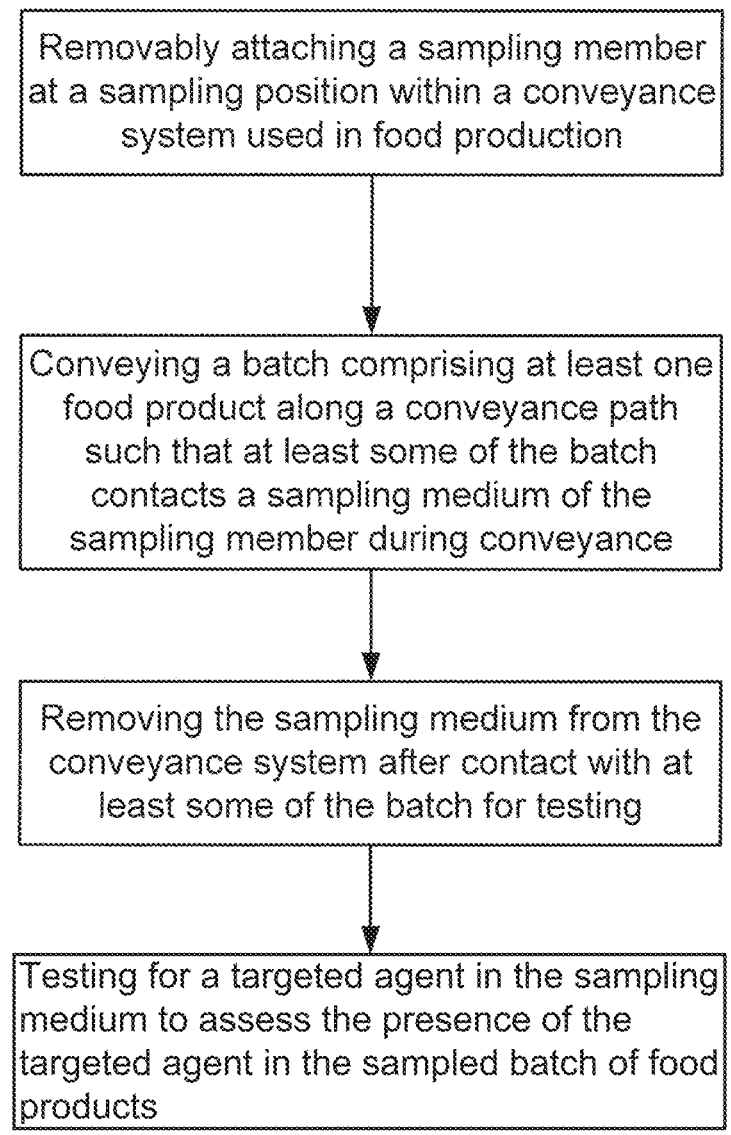
Figure 19:
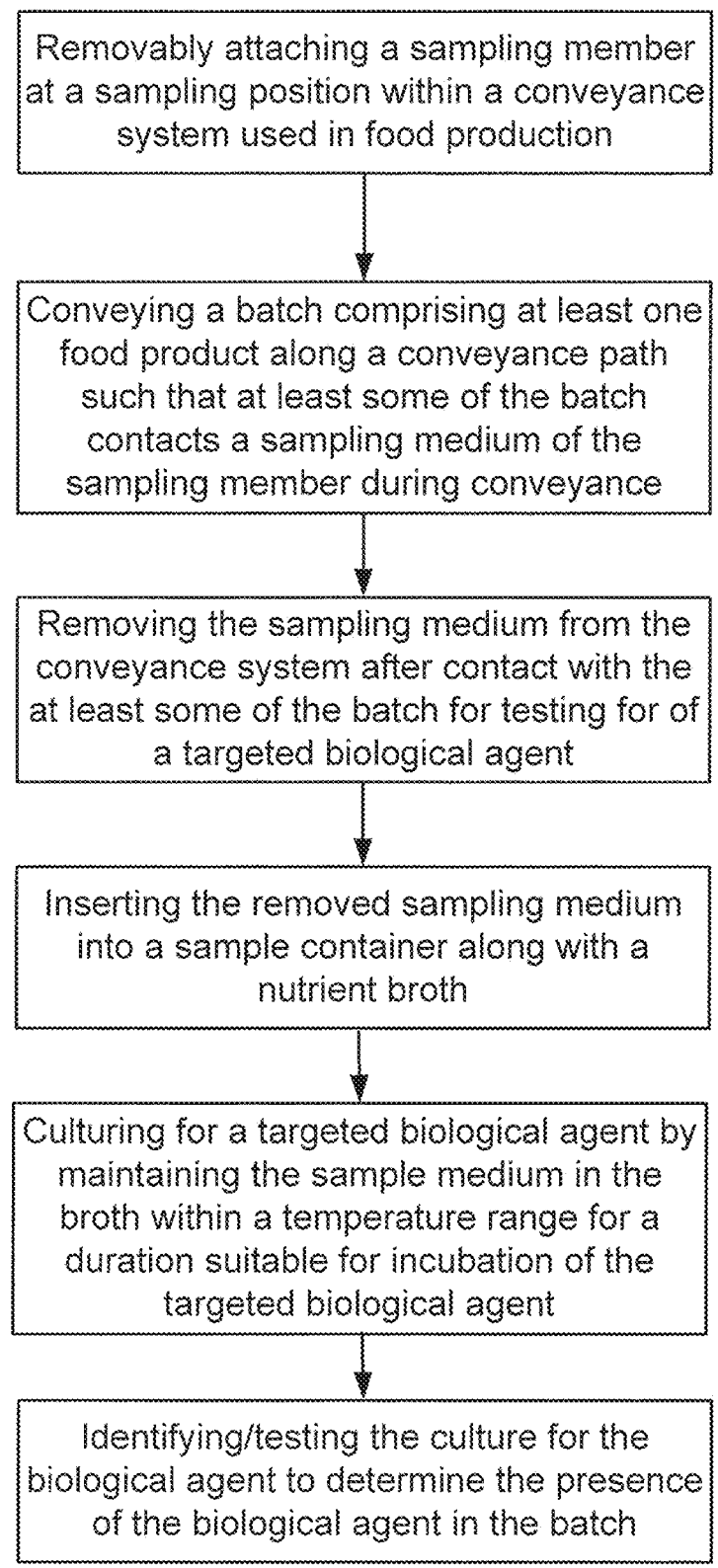

FIGS. 17-19 schematically illustrate methods of batch sampling for a targeted agent in accordance with embodiments of the present invention. As described previously, these methods can be applied to a variety of differing industries for use in detection of varying different agents.

In the example embodiment of FIG. 17, the method comprises: removably attaching a sampling member within a conveyance system at a sampling position; conveying a batch comprising at least one item along a conveyance path such that at least one portion of the batch contacts a sampling medium of the sampling member during conveyance along a conveyance path of the conveyance system; removing the sampling medium from the conveyance system after contact with the at least one portion of the batch for testing for the targeted agent and testing the targeted agent using the sampling medium to assess a presence of the targeted agent within the batch. It is appreciated that this approach can be utilized for batch testing of a number of different products conveyed along a conveyance path and collected in a batch. Although this approach is particularly useful for batch sampling of food product, such as beef trimmings, it may also be used for sampling of industrial products, packages being shipped, luggage being loaded onto a commercial airliner, or any number of applications. In such applications, the targeted agent may be any number of things, including contaminants, such as heavy metals, mold, chemicals or pesticides or any prohibited substance, such as narcotics or explosive residue.

In some methods, the targeted agent is a biological agent that may be present in a food product being conveyed and collected in a batch. The system and methods may be used in food production where a batch of food items are conveyed by the conveyance system. In such methods, the sampling may determine the presence of a biological agent within the food products, including various types of bacteria, mold, and pathogens.

As shown in FIG. 18, the method may include removably attaching a sampling member at a sampling position within a conveyance system used in food production, typically a conveyor belt; conveying a batch comprising at least one food product along a conveyance path such that at least some of the batch contacts a sampling medium of the sampling member during conveyance; removing the sampling medium from the conveyance system after contact with at least some of the batch for testing; and testing for the targeted agent in the sampling medium to assess the presence of the targeted agent in the sampled batch of food products.

In such applications, testing comprises culturing for the biological agent (for example, bacterium, virus, fungus, and pathogens, such as E. *Coli*) with the sampling medium, such as shown in the method of FIG. 19. After sampling of the batch utilizing one or more sampling devices positioned in a sampling position within the conveyance system, the sample mediums of the devices may be cultured to identify whether the targeted biological agent is present. Culturing for the biological agent generally includes: adding a nutrient broth to the exposed sampling medium; maintaining the sampling medium soaked in the nutrient broth at a temperature within a temperature range suitable for growth of the biological agent for a duration of time suitable for incubation of the biological agent; and testing/identifying whether the biological agent is present within the culture.

FIG. 20 illustrates a method of assembling a sampling device in accordance with embodiments of the invention. The method includes steps of: removably attached a sampling member comprising a compressed, dried cellulose sheet member to a support plate; securing the support plate with the sampling member mounted thereon to a base plate affixed to a conveyor such that the sampling member is disposed along the conveyance path of the conveyor so as to contact products conveyed along the path for sampling; and conveying a product stream along the conveyance path until an entire batch has been conveyed, then removing the sample member from the support plate. The sample member is then inserted into a sample container along with nutrient broth and cultured for the target analyte for testing and identification as set forth in the methods described above. In one aspect, removably attaching the sampling member and securing the support plate to the base plate may be performed in accordance with any of the embodiments described above.

To assess the effectiveness and ease of use of differing types of sample collection devices in accordance with certain embodiments, testing was conducted using different types of sample collection devices along a single conveyor system. Five sample collection devices were fashioned to work in concert with a commercial style trim conveyor using an open hinge flat top, flush edge, acetal conveyor belt (Intralox Series 800). The devices consisted of a filament sampling device 40, a sampling roller device 30, a front end sponge device 20, an underside sponge device (not shown), and a fluid spray device (not shown). The filament sampling device included a cotton string mop head (M) set over the belt that would drag over the beef trim as it passed by. The sampling roller device included a foam roller with an outer gauze sleeve that contacts the beef trimming as the roller rolls over the passing trim. The front end sponge device 20 consisted of a sponge affixed at the front end of the conveyor where the trim pieces contact before dropping into the combo bin that collects each batch. The underside sponge (U) included a sponge placed in contact with the underside (U) of the belt to collect any material remaining on the belt, and the fluid spray device (W) was a mister positioned to mist the trim pieces with water as they fell from the conveyor into the combo bin. The water was collected from the bottom of the bin once the batch was collected.

To process the samples, the mop heads were placed into sterile poly bags with 400 ml of a nutrient broth, tryptic soy broth (TSB). The gauze sleeves from the foam rollers were placed into sterile whirlpak bags with 100 ml of TSB. The front end sponges and the underside sponges were placed in whirlpak bags with 200 ml of TSB. Water from the combo bin was collected with two sterile cellulose sponges and placed in whirlpak bags with 100 ml of TSB. The samples were then collected and cultured to allow incubation of any bacterial agents recovered in the samples. All samples were incubated at 42° C. for 12 h then held at 4° C. until processing the next day.

Following incubation, the samples were processed by immunomagnetic separation, in which 1 ml from each enrichment was subjected to anti-O157 immunomagnetic bead cell concentration (Dynal, Invitrogen). Fifty microliters of the final bead-bacteria complexes were spread-plated onto ntChromagar (CHROMAgar-O157 [DRG International] supplemented with novobiocin [5 mg/liter; Sigma] and potassium tellurite [2.5 mg/liter; Sigma]). All plates were incubated at 37° C. for 18 to 20 h. After the plates were incubated, up to three suspect colonies were picked and tested by latex agglutination (DrySpot E. coli O157; Oxoid).

Initial trials were conducted to determine the limit of detection for each type of sampling collection device. These trials were performed in a best case format where 50 lb of 50/50 beef trim were placed onto the trim conveyor and conveyed off the end of the table into a catch bin then an inoculated trim piece was placed on the conveyor and samples were collected. This was done to simulate the normal flow of trim and to expose the test detection methods to fat build up and the background microflora associated with fresh beef trim. After the uninoculated 50 lb had been collected, the inoculated piece of beef trim was placed on the conveyor and passed through the various detection apparatus in a manner where it was known that the inoculated pieces came into contact with each sampling device. Inoculation levels of $10^4$ and $10^3$ CFU/piece of beef trim were used. For trials using the $10^4$ CFU inoculation level, all detection methods were positive on each of 6 replicates (Table 1). For the $10^3$ CFU inoculation trial, the filament, roller and front sponge devices each recovered E. coli O157:H7 on every sample, while the underside sponge device underneath the belt recovered E. coli O157:H7 from half of the samples (Table 1). From these results, inoculation levels of $10^3$ CFU were chosen for future trials.

TABLE 1

Preliminary E. coli O157 detection trial percent positive*

| Inoculation level | Number of samples | Mop | Roller | Front sponge |
|---|---|---|---|---|
| $3 \times 10^4$ CFU | 6 | 100 | 100 | 100 |
| $3 \times 10^3$ CFU | 6 | 100 | 100 | 100 |

*Inoculation was applied to one trim piece.

For the remaining trials, inoculated trim pieces were not kept separate from the remaining 50 lb of uninoculated trim. Instead, the inoculated trim piece was inserted randomly into a 50 lb batch of 50/50 trim and placed onto the trim conveyor. The average inoculation across all trials was $3 \times 10^3$ CFU/50 lb of trim, which is equivalent to 0.13 CFU/g. Results indicated that the filament sampling device and front sponge devices had the highest detection rates for E. coli O157:H7, with each exceeding 60% (see Table 2).

TABLE 2

E. coli O157: H7 detection by culture**

| | Filament | Roller | Front sponge | Water |
|---|---|---|---|---|
| % positive | 73 | 29 | 61 | 44 |

N = 41 for M, R, F, and U
N = 18 for W
**Fifty pounds of 50/50 beef trim were used for each replicate. Average inoculation was $3 \times 10^3$ CFU.

The results indicated that the roller and underside sponge devices did not perform at acceptable rates of detection with neither exceeding 30% positive. The water application provided a somewhat higher detection ability, but still did not exceed 50%. When non-O157 STEC detection was evaluated, the filament and front sponge devices were considerably more effective at detecting the targeted agent than the other devices tests (see Tables 3A-3B).

TABLE 3

Non-O157 STEC (O103, O111, O145) detection by PCR

| Sampler Type | Filament | Roller | Front sponge | Water |
|---|---|---|---|---|
| % positive | 82 | 38 | 70 | 27 |

N = 60 for M, R, F, and U
N = 36 for W

Through these trials, it was determined which of these nondestructive sample devices and methods provides the most reliable detection of bacterial pathogens associated with beef trim. This work also provides a proof of concept that these methods work under industrial conditions and provide samples representative of the entire trim lot instead of a localized representation as is the case with the currently used N-60 method.

While the above embodiments illustrate use of the invention in batch sampling of food products, particularly meat trimming, it is appreciated that various embodiments may be utilized in various other applications where items are processed in a batch. For example, in a manufacturing application, it may be desirable to sample a batch of raw or processed material to detect the presence of a contaminant that may render the batch unsuitable for further manufacture or for sale to the consumer. In yet another application, shipments of goods for commercial or travel purposes, it may be desirable to sample commercial goods or other items, such as luggage, that are collected in batches for shipment and transport by various by vehicle or aircraft for various targeted agents, such as explosive residue.

In the above description, various embodiments of the present invention have been described. For purposes of explanation, specific configurations and details are set forth in order to provide a more thorough understanding of the invention. However, it will also be apparent to one skilled in the art, that the present invention may be practiced without various specific details. For example, well known features may be omitted or simplified in order not to obscure the embodiment being described.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

In addition to the example embodiment are described herein, various other embodiments may become apparent to those of ordinary skill in the art upon reading the foregoing description. Accordingly, this invention includes all modifications and equivalents of the features and methods described herein. Moreover, any combination of the elements described above in all possible variations thereof is encompassed by the invention unless indicated otherwise.

What is claimed is:

1. A sampling device for sampling a plurality of items conveyed by a conveyance system to a front end of a conveyor belt of the conveyance system, the sampling device comprising:
    a sampling pad or sheet having a porous surface configured to retain a solid residue and/or absorbs a liquid residue of at least some of the plurality of items conveyed by the conveyance system upon contact with the porous surface, wherein the sampling pad or sheet has a length and a width, the length being greater than the width;
    a base plate having a length and a width, the length of the base plate being greater than the width of the base plate, wherein the base plate extends length-wise between opposing ends of the base plate, each end having a coupling mechanism configured for attaching to the conveyance system; and
    a support plate having one or more attachment features that interface with one or more corresponding attachment features of the base plate thereby fixedly attaching the support plate to the base plate, wherein the support plate underlies the sampling pad or sheet the support plate having a length and a width, the length of the support plate being greater than the width of the support plate, wherein the length of the support plate is the same or greater than the length of the sampling pad or sheet, wherein the support plate is attached to the sampling pad or sheet such that the sampling pad or sheet is held in a stationary sampling position relative the base plate and support plate,
    wherein the sampling pad or sheet is removable from the support plate to allow testing of the sampling pad or sheet and replacement of the sampling pad or sheet,
    wherein the support plate is releasably attachable to the base plate to facilitate removal for cleaning.

2. The sampling device of claim 1, further comprising:
    a conveyance system comprising a conveyor belt and configured to convey the plurality of items along a conveyance path extending partly along the conveyor belt,
    wherein the base plate is attached to a front end of the conveyance system along the conveyance path to allow sampling of the plurality of items conveyed along the conveyance path by the conveyance system.

3. The sampling device of claim 2, wherein the conveyance system is configured with food contact surfaces to convey food products.

4. The sampling device of claim 2, wherein the base plate is mounted to the conveyance system and configured such that the sampling pad or sheet is not in contact with the conveyor belt.

5. The sampling device of claim 1, wherein the sampling pad or sheet is rectangular.

6. The sampling device of claim 5, wherein the length of the sampling pad or sheet is between 6 inches and 36 inches and the width of the sampling pad or sheet is between 0.5 inches and 12 inches.

7. The sampling device of claim 1, wherein the sampling pad or sheet having the porous surface comprises a material selected from the group consisting of: a sponge, a cloth and a gauze.

8. The sampling device of claim 1, the sampling pad or sheet comprising a cloth.

9. The sampling device of claim 1, wherein the one or more attachment features and one or more corresponding attachment features comprises interfacing slots between the support plate and the base plate.

10. The sampling device of claim 1, further comprising a snap-fit coupling, wherein the sampling pad or sheet is attached to the support plate by the snap-fit coupling.

11. The sampling device of claim 1, further comprising:
    wherein the sampling pad or sheet cloth is foldable to be configured to be contained within a resealable biological sampling bag.

12. A method of sampling for a targeted agent, said method comprising:
    providing a sampling device as in claim 1 mounted on a conveyance system at a stationary sampling position;
    conveying a plurality of items along a conveyance path of the conveyance system such that at least some of the plurality of items contact the sampling pad or sheet while the sampling device and sampling pad or sheet are in the respective stationary sampling positions during conveyance along the conveyance path of the conveyance system; and
    removing the sampling pad or sheet from the sampling device after contact with the at least some of the plurality of items for testing for the targeted agent.

13. The method of claim 12, further comprising:
    testing the sampling pad or sheet medium for the targeted agent to assess a presence of the targeted agent within the plurality of batch of items.

14. The method of claim 13, wherein the targeted agent is a biological agent and wherein testing comprises culturing the sampling pad or sheet to identify if the biological agent is present.

15. The method of claim 14, wherein the culturing comprises:
    adding a nutrient broth to the sampling pad or sheet medium;

maintaining the sampling pad or sheet soaked in the nutrient broth at a temperature within a temperature range suitable for growth of the biological agent for a time period suitable for incubation or reproduction of the biological agent; and testing/identifying whether the biological agent is present in the broth.

16. The method of claim 13, wherein testing the sampling pad or sheet for the targeted agent utilizes spectroscopy.

17. The method of claim 12, wherein the plurality of items at least one item comprises a plurality of food items.

18. The method of claim 17, wherein the plurality of food items comprises a plurality of meat cuts or products.

19. The method of claim 18, wherein the plurality of meat cuts comprises beef cuts.

20. The method of claim 19, wherein the targeted agent comprises *E. coli*.

21. The method of claim 12, wherein the targeted agent comprises a biological agent, contaminant, chemical or other compound.

22. The method of claim 21, wherein the targeted agent comprises a pathogen.

23. The method of claim 12, wherein the surface of the sampling pad or sheet medium retains the liquid and/or solid residue by absorption and/or adsorption, respectively.

24. The method of claim 12, wherein the sampling pad or sheet medium comprises a cellulose sponge material without biocides.

25. The method of claim 12, further comprising:

replacing the sampling pad or sheet medium with an additional sampling pad or sheet.

26. A sampling device for sampling a plurality of products conveyed by a conveyance system, the sampling device comprising:

a sampling pad or sheet having a porous sampling surface configured to retain a solid residue and/or absorbs a liquid residue of the plurality of products upon contact;

a base having a length and a width, the length being greater than the width, wherein the base has a channel extending lengthwise between opposite ends of the base, wherein the channel includes a planar support portion supporting the sampling pad or sheet thereon, wherein each of the opposite ends of the base has a coupling mechanism configured to attach to the conveyance system, a frame fitted over the sampling pad or sheet and coupled to the base by sliding into the channel of the base thereby maintaining the sampling pad or sheet between the frame and the planar support portion in a stationary sampling position relative the frame and the base, wherein the frame includes one or more windows through which a majority of the porous sampling surface of the sampling pad or sheet remains exposed through the frame to allow sampling while maintained in the stationary sampling position.

27. The sampling device of claim 26, further comprising:

a conveyance system comprising a conveyor belt and configured to convey the plurality of products along a conveyance path extending partly along the conveyor belt, wherein the base is attached to a front end of the conveyance system along the conveyance path to allow sampling of the plurality of products conveyed along the conveyance path by the conveyance system.

28. The sampling device of claim 27, wherein the conveyance system is configured to convey food products by utilizing food contact surfaces for conveying the food products.

29. The sampling device of claim 27, wherein the base is mounted to the conveying system and configured such that the sampling pad or sheet is not in contact with the conveyor belt.

30. The sampling device of claim 26, wherein the sampling pad or sheet is rectangular.

31. The sampling device of claim 30, wherein the sampling pad or sheet has a length between 6 inches and 36 inches and a width between 0.5 inches and 12 inches.

32. The sampling device of claim 26, wherein the sampling pad or sheet comprises a material selected from the group consisting of: a sponge, a cloth and a gauze.

33. The sampling device of claim 26, wherein the sampling pad or sheet comprising a cloth.

34. The sampling device of claim 26, further comprising:

wherein the sampling pad or sheet cloth is foldable to be configured to be contained within a resealable biological sampling bag.

35. A sampling device for sampling a plurality of products conveyed by a conveyance system, the sampling device comprising:

a sampling pad or sheet having a porous surface configured to retain a solid residue and/or absorbs a liquid residue of the plurality of products upon contact with the plurality of products being conveyed;

a base having a length and width, the length being longer than the width, wherein the base extends lengthwise between opposite ends of the base and includes a planar support portion underlying the sampling pad or sheet; and an overlay frame that is attached to the base and fitted over the planar support portion with the sampling pad or sheet disposed between the overlay frame and the planar support portion, wherein the overlay frame includes one or more latches fixedly attached to the base, wherein the overlay frame overlays multiple edges of the sampling pad or sheet and maintains the sampling pad or sheet in a stationary sampling position relative the overlay frame and the base, wherein the one or more latches are releasable to allow release of the overlay frame and removal of the sampling pad or sheet.

36. The sampling device of claim 35, wherein the sampling pad or sheet is substantially and the base are each rectangular in shape, and wherein the overlay frame is dimensioned such that the overlay frame overlaps three edges of the sampling pad or sheet thereby maintaining the sampling pad or sheet in the stationary sampling position relative the overlay frame and base to allow stationary sampling.

37. The sampling device of claim 35, further comprising:

a conveyance system comprising a conveyor belt and configured to convey the plurality of products along a conveyance path extending partly along the conveyor belt, wherein the base is attached to a front end of the conveyance system along the conveyance path to allow sampling of the plurality of products conveyed along the conveyance path by the conveyance system.

38. The sampling device of claim 35, further comprising:
wherein the sampling pad or sheet cloth is foldable to be configured to be contained within a resealable biological sampling bag.

* * * * *